US011353459B2

(12) United States Patent
Adams et al.

(10) Patent No.: US 11,353,459 B2
(45) Date of Patent: Jun. 7, 2022

(54) METHODS OF USING PD-L1 EXPRESSION IN TREATMENT DECISIONS FOR CANCER THERAPY

(71) Applicant: Creatv MicroTech, Inc., Potomac, MD (US)

(72) Inventors: Daniel Adams, Basking Ridge, NJ (US); Cha-Mei Tang, Potomac, MD (US)

(73) Assignee: CREATV MICROTECH, INC., Potomac, MD (US)

( * ) Notice: Subject to any disclaimer, the term of this patent is extended or adjusted under 35 U.S.C. 154(b) by 15 days.

(21) Appl. No.: 16/092,998

(22) PCT Filed: Apr. 14, 2017

(86) PCT No.: PCT/US2017/027714
§ 371 (c)(1),
(2) Date: Oct. 11, 2018

(87) PCT Pub. No.: WO2017/181073
PCT Pub. Date: Oct. 19, 2017

(65) Prior Publication Data
US 2019/0128892 A1 May 2, 2019

Related U.S. Application Data

(60) Provisional application No. 62/322,570, filed on Apr. 14, 2016.

(51) Int. Cl.
A61K 45/06 (2006.01)
A61P 35/00 (2006.01)
G01N 33/574 (2006.01)
A61K 39/395 (2006.01)
C07K 16/28 (2006.01)

(52) U.S. Cl.
CPC . *G01N 33/57492* (2013.01); *A61K 39/39558* (2013.01); *A61K 45/06* (2013.01); *C07K 16/2827* (2013.01); *C07K 2317/76* (2013.01); *G01N 2333/70532* (2013.01)

(58) Field of Classification Search
CPC ........ G01N 33/57492; A61K 39/39558; C07K 16/2827
USPC ...................................................... 435/7.23
See application file for complete search history.

(56) References Cited

U.S. PATENT DOCUMENTS 10,871,491 B2 * 12/2020 Tang .................... C12Q 1/6886
2013/0309250 A1    11/2013 Cogswell et al.
2018/0318347 A1 * 11/2018 Buell ................... A61K 31/495

FOREIGN PATENT DOCUMENTS

WO    2016/033103    3/2016
WO    2016/061064    4/2016

OTHER PUBLICATIONS

Heeren et al. (OncoImmunology, 4: 6, e1009296, Jun. 2015, pp. 1-3).*
International Search Report and Written Opinion of the International Searching Authority, dated Jul. 20, 2017 in corresponding International Patent Application No. PCT/US17/27714.
Mazel et al., "Frequent expression of PD-L1 on circulating breast cancer cells", Molecular Oncology, 9: 1773-1782 (2015).
Lin et al., "MINI02.04 Sequential Assessment of DNA Damage Response and PD-L1 Expression in Circulating Tumor Cells of Lung Cancer Patients during Radiotherapy", Journal of Thoracic Oncology, 10(9): S266-S267 (2015).
Krupa et al., "Characterization of programmed cell death-1 ligand (PD-L1) expression in circulating tumor cells (CTCs) of lung cancer", J. Thoracic Oncology, vol. 11, No. 25, Suppl. 552 (2016).
Boffa et al., "Cellular Expression of PD-L1 in the Peripheral Blood of Lung Cancer Patients is Associated with Worse Survival", Cancer Epidemiol Biomarkers Prev. Published online Apr. 26, 2017. Doi: 10.1158/1055-9965.EPI-17-0120. pp. 1-26.
Schildberg, F.A. et al. "Stromal Cells in Health and Disease", 2018, Cytometry Part A, 93A:871-875.
Pittet, M.J. et al., "The journey from stem cell to macrophage", 2014, Ann. NY Acad. Sci. 1319(1): 1-18.
Notice of Preliminary Rejection dated Jun. 8, 2021 in Korean Application No. 10-2018-7032222 with English translation.
Arun Rajan et al., "Nivolumab (anti-PD-1, BMS-936558, ONO-4538) in patients with advanced non-small cell lung cancer", Translational Lung Cancer Research, vol. 3, No. 6, 2014, pp. 403-405.

* cited by examiner

Primary Examiner — Yan Xiao
(74) Attorney, Agent, or Firm — Wenderoth, Lind & Ponack, L.L.P.

(57) ABSTRACT

Methods of using detection of PD-L1 expression by circulating cancer cells in the screening, monitoring, treatment and diagnosis of cancer in subjects are disclosed. The methods are based on assaying one or more of circulating tumor cells (CTCs), epithelial to mesenchymal transition CTCs (EMTCTCs), cancer associated macrophage-like cells (CAMLs), and cancer associated vascular endothelial cells (CAVEs) isolated from a subject having cancer for PD-L1 expression.

17 Claims, 15 Drawing Sheets
(14 of 15 Drawing Sheet(s) Filed in Color)

| ID# | TC (%/SI) | 22c3 (%/SI) | 28-8 (%/SI) |
|---|---|---|---|
| 1 | 17/2 | 0 | 0 |
| 2 | 100/3 | 0 | 0 |
| 3 | 33/1 | 0 | 0 |
| 4 | 100/1 | 0 | 0 |
| 5 | 33/1 | 0 | N/A |
| 6 | N/A | 0 | 0 |
| 7 | 50/2 | 0 | 0 |
| 8 | 33/2 | 10/1+ | 20/2+ |
| 9 | 80/3 | 40/2+ | 80/3+ |
| 10 | 25/0 | N/A | N/A |
| 11 | 100/0 | N/A | N/A |
| 12 | 100/0 | N/A | N/A |
| 13 | 100/0 | N/A | N/A |
| 14 | 51/1 | N/A | N/A |
| 15 | 100/1 | N/A | N/A |
| 16 | 50/1 | N/A | N/A |
| 17 | 13/1 | N/A | N/A |
| 18 | 100/1 | N/A | N/A |
| 19 | 50/1 | N/A | N/A |
| 20 | 100/1 | N/A | N/A |
| 21 | 86/1 | N/A | N/A |
| 22 | 75/1 | N/A | N/A |
| 23 | 50/1 | N/A | N/A |
| 24 | 100/1 | N/A | N/A |
| 25 | 100/1 | N/A | N/A |
| 26 | 50/1 | N/A | N/A |
| 27 | 75/2 | N/A | N/A |
| 28 | 20/2 | N/A | N/A |
| 29 | 100/2 | N/A | N/A |
| 30 | 72/2 | N/A | N/A |
| 31 | 100/2 | N/A | N/A |
| 32 | 100/2 | N/A | N/A |
| 33 | 4/3 | N/A | N/A |
| 34 | 13/3 | N/A | N/A |
| 35 | 100/3 | N/A | N/A |
| 36 | 100/0 | N/A | N/A |
| 37 | N/A | N/A | N/A |
| 38 | N/A | N/A | N/A |
| 39 | N/A | N/A | N/A |
| 40 | N/A | N/A | N/A |
| 41 | N/A | N/A | N/A |

METHODS OF USING PD-L1 EXPRESSION IN TREATMENT DECISIONS FOR CANCER THERAPY

BACKGROUND OF INVENTION

Cancer is the second leading cause of death in the United States, and 42% of men and 38% of women will develop cancer in their lifetimes[51-54]. Immunotherapy harnesses a patient's own immune system to attack cancer, irrespective of the origin. The immune system is regulated by a network of checks and balances that evolved to attack foreign invaders like bacteria and viruses. However, cancer can evade the immune system by expressing proteins, such as PD-L1 and PD-L2, which inhibit the immune system from attacking cancer cells.

In particular, interactions between tumor cells and T cells involve contact between the major histocompatibility complexes (MHC) on tumor cells and the T cell receptor (TCR) on T cells[54]. Upon contact between the MHC and T cell receptor, the T cells are activated and the tumor cells are destroyed.

Tumor cells can evade T cell immunosurveillance if they expresses the immune checkpoint protein PD-L1 on their surface. When present, PD-L1 binds to PD-1 expressed by T cells and activation of the T cell is blocked, thus suppressing T cell immunosurveillance.

Immune checkpoint inhibitors have been developed that can block the PD-L1/PD-1 interaction. Such drugs permit the T cell immunosurveillance mechanism to again function normally, and tumor cells can thus be destroyed through the normal immune response in the subject.

Blockage of CTLA-4 on T cells can have a similar effect. The first immunotherapeutic based on CTLA-4 was approved by the FDA for melanoma in 2011. The pace of FDA immunotherapy approvals increased in 2014 and by the end of 2016, there were 18 immunotherapy approvals for melanoma, non-small cell lung cancer (NSCLC), renal cell carcinoma (RCC), head and neck cancer, bladder cancer and Hodgkin's lymphoma[55-59]. There are currently more than 100 open immunotherapy clinical trials indicating potential for broad efficacy across multiple tumors.

The key to the effective use of immune checkpoint inhibitors is determining whether a particular subject having cancer will respond to the drugs. If an antibody which binds to PD-L1 or PD-1 and that serves as an immune checkpoint inhibitor is administered to a patient whose tumor cells do not express PD-L1, the treatment will be ineffective. As such antibody-based treatments are very expensive, it is important to have at least some indication that the patient will respond to the treatment.

Obtaining cancer cells via tumor biopsies for PD-L1 expression surveys has serious drawbacks that include pain and discomfort to patients, the inability to survey more than an isolated area of the tumor, and the potential for protein expression profiles to changes to occur over time in the tumor microenvironment.

Blood-based biopsies are an improvement on tissue biopsies in that they can provide real time sequential tracking of cells shed by the tumor or that otherwise break-off. Blood samples can be more easily obtained, and obtained more often from a patient. Further, changes in protein expression profiles can be monitored over time. Circulating tumor cells (CTCs) are one cancer-associated cell type that can easily be isolated from the peripheral blood and that can be used as a substitute for tumor cells obtained from tissue biopsies[1-4]. CTCs are tumor cells broken off from the solid tumors into the blood stream. CTCs can be found in blood of carcinomas, sarcomas, neuroblastomas and melanomas patients.

The identification of additional cell types that can be obtained from blood-based biopsies will critical to further develop use of this technique for identifying cancer patients that will benefit from treatment with immune checkpoint inhibitors.

The present invention is directed to providing effective means for determining whether a subject having cancer will benefit from treatment with immune checkpoint inhibitors, as well as other important goals.

BRIEF SUMMARY OF INVENTION

The invention relates to peripherally-based biomarkers and the cells that express them for use in the screening, monitoring, and diagnosis of cancer in a subject. The invention also relates to methods of treating cancer based on the presence or absence or change in expression of the biomarkers. The methods defined herein will allow oncologists to select better combinations and sequences of conventional cytotoxic and immunotherapies, as well as identify patients likely to show durable responses to immunotherapy.

In a first embodiment, the invention is drawn to methods of screening a subject having cancer for susceptibility to an immune checkpoint inhibitor. The method comprises assaying one or more of circulating tumor cells (CTCs), epithelial to mesenchymal transition CTC cells (EMTCTCs), cancer associated macrophage-like cells (CAMLs), and cancer associated vascular endothelial cells (CAVEs) isolated from a subject having cancer for PD-L1 expression, wherein when PD-L1 expression is detected, the subject is deemed susceptible to an immune checkpoint inhibitor.

In a second embodiment, the invention is drawn to methods of predicting responsiveness of a subject having cancer to treatment with an immune checkpoint inhibitor. The method comprises assaying one or more of CTCs, EMTCTCs, CAMLs, and CAVEs isolated from a subject having cancer for PD-L1 expression, wherein when PD-L1 expression is detected, the subject is predicted to be responsive to treatment with an immune checkpoint inhibitor.

In a third embodiment, the invention is drawn to methods for selecting a treatment for a subject having cancer. The method comprises assaying one or more of CTCs, EMTCTCs, CAMLs, and CAVEs isolated from a subject having cancer for PD-L1 expression, wherein when PD-L1 expression is detected, administration of a therapeutically effective amount of an immune checkpoint inhibitor to the subject is selected as a treatment for the subject.

In a fourth embodiment, the invention is drawn to assays for identifying a subject having cancer to receive an immune checkpoint inhibitor treatment. The method comprises assaying one or more of CTCs, EMTCTCs, CAMLs, and CAVEs isolated from a subject having cancer for PD-L1 expression, wherein when PD-L1 expression is detected, the subject is identified as a subject to receive an immune checkpoint inhibitor treatment.

In a fifth embodiment, the invention is drawn to methods of treating a subject having cancer. The method comprises (a) assaying one or more of CTCs, EMTCTCs, CAMLs, and CAVEs isolated from a subject having cancer for PD-L1 expression, and (b) administering a therapeutically effective amount of an immune checkpoint inhibitor to the subject when PD-L1 expression is detected.

In a sixth embodiment, the invention is drawn to methods of treating a subject having cancer. The method comprises administering a therapeutically effective amount of an immune checkpoint inhibitor to a subject having cancer, wherein said immune checkpoint inhibitor is administered after PD-L1 expression is detected in one or more of CTCs, EMTCTCs, CAMLs, and CAVEs isolated from the subject having cancer.

In a seventh embodiment, the invention is drawn to methods of monitoring PD-L1 expression in a subject having cancer. The method comprises (a) assaying one or more of CTCs, EMTCTCs, CAMLs, and CAVEs isolated at a first time point from a subject having cancer for PD-L1 expression, (b) assaying one or more of CTCs, EMTCTCs, CAMLs, and CAVEs isolated at a second time point from a subject having cancer for PD-L1 expression, and (c) comparing PD-L1 expression assayed in the cells isolated at the first and the second time points. In particular aspects of this embodiment, the subject is undergoing treatment for cancer.

In an eighth embodiment, the invention is drawn to methods of monitoring treatment in a subject having cancer. The method comprises (a) assaying one or more of CTCs, EMTCTCs, CAMLs, and CAVEs isolated at a first time point from a subject undergoing treatment for cancer for PD-L1 expression, (b) assaying one or more of CTCs, EMTCTCs, CAMLs, and CAVEs isolated at a second time point from a subject undergoing treatment for cancer for PD-L1 expression, and (c) comparing PD-L1 expression assayed in the cells isolated at the first and the second time points, thereby monitoring treatment in a subject having cancer. In particular aspects of this embodiment, the subject is being treated using an immune checkpoint inhibitor.

In certain of the relevant embodiments and aspects defined above, the immune checkpoint inhibitor is one or more of a PD-L1 antagonist, PD-1 antagonist, and a CTLA-4 antagonist.

In certain of the relevant embodiments and aspects defined above, the immune checkpoint inhibitor inhibits one or more of (i) binding between PD-L1 and PD-1, (ii) binding of PD-L1 to its binding partners, (iii) binding of PD-1 to its binding partners, and (iv) binding of CTLA-4 to its binding partners.

In certain of the relevant embodiments and aspects defined above, the immune checkpoint inhibitor is an antibody, such as a monoclonal antibody. In particular aspects, the immune checkpoint inhibitor is a human antibody, a humanized antibody, or a chimeric antibody.

Examples of specific immune checkpoint inhibitors include, but are not limited to, one or more of Nivolumab (Opdivo), Ipilimumab (Yervoy), Pembrolizumab (Keytruda), Atezolizumab (Tecentriq), Tremelimumab, and Durvalumab (MED14736).

In certain of the relevant embodiments and aspects defined above, the methods further comprise administering a therapeutically effective amount of one or more additional anti-cancer agents to the subject. The additional anti-cancer agents include, but are not limited to, immunotherapeutic agents, chemotherapeutic agents, radiotherapeutic agents, existing cancer drugs, CCR5 and CXCR4.

Examples of specific anti-cancer agents include, but are not limited to, one or more of T-VEC, AM-0010, CXCR4 antagonist, TGF-beta kinase inhibitor galunisertib, anti-CSF-1R monoclonal antibody, Abemaciclib, Faslodex, necitumumab, AZD9291, Cyramza (ramucirumab), TPIV 200, Galunisertib, cancer vaccines, cytokines, cell-based therapies, bi- and multi-specific antibodies, tumor-targeting mAbs, Rituximab, oncolytic viruses, reovirus, Blinatumomab, Sipuleucel-T, T-Vec, IL-2, IFN-α, Trastuzumab, Celuximab, bevacizumab, Tim-3, BTLA, anti-IL-10, GM-CSF, anti-angiogenesis treatment, VEGF blockade, HMGB1, Nrp1, TAM receptor tyrosine kinases, Axl, MerTK, ALT-803, IL-15, Immunosuppressive Ligand Phosphatidylserine (PS), bavituximab, bevacizumab (anti-VEGF), coblmetinib (MEK inhibitor), vemurafenib (BRAF inhibitor), erlotinib (EGFR), alectinib (ALK inhibitor), bevacizumab (anti-VEGF), pazopanib (tyrosine kinase inhibitor), dabrafenib (BRAF inhibitor), trametinib (MEK inhibitor), durvalumab (anti-PD-L1), sunitinib (RTK inhibitor), pazopanib (RTK inhibitor), sargramostim, VISTA, TIM-3, LAG-3, PRS-343, CD137 (4-1BB)/HER2 bispecific, USP7, anti-HER2, SEMA4D, CTLA-4, PD-1, PD-L1, and PD-L2.

In certain of the relevant embodiments and aspects defined above, the assaying for PD-L1 expression may be by one or more of detecting PD-L1 protein expression or detecting PD-L1 mRNA production. PD-L1 protein expression may be detected, for example, via immunohistochemistry (IHC). IHC may be performed by membrane staining, cytoplasmic staining, or a combination thereof. IHC may be performed using an anti-PD-L1 antibody, i.e. an antibody having binding specificity for PD-L1. PD-L1 protein expression may be detected as a weak staining intensity by IHC, moderate staining intensity, or strong staining intensity. PD-L1 protein expression may also be detected as a low staining intensity by IHC, moderate staining intensity, or high staining intensity. PD-L1 protein expression may also be detected as inducible from low staining intensity to high staining intensity, or inducible from low staining intensity to moderate staining intensity, or inducible from moderate staining intensity to high staining intensity. PD-L1 protein expression may be detected as any staining of the isolated cells.

In certain aspects, IHC is performed using immunofluorescence (IF) staining where one or more antibodies with binding specificity for PD-L1 are utilized. Binding of the anti-PD-L1 antibody to PD-L1 may be detected via a fluorescent compound conjugated to the anti-PD-L1 antibody or it may be detected via a detectable label-conjugated secondary antibody with binding specificity for the anti-PD-L1 antibody. Suitable detectable labels include fluorophores.

In certain of the relevant embodiments and aspects defined above, PD-L1 expression is detected when the level of PD-L1 expression is greater than PD-L1 expression is a population of stromal cells from a subject of the same species that does not have cancer.

In certain of the relevant embodiments and aspects defined above, CTCs, EMTCTCs, CAMLs, and CAVEs are isolated from blood obtained from the subject having cancer. In certain aspects, the blood is peripheral blood.

In certain of the relevant embodiments and aspects defined above, the subject having cancer may be undergoing treatment using one or more of a targeted agent, chemotherapy, or radiation therapy.

In certain of the relevant embodiments and aspects defined above, the cancer is a lung cancer, breast cancer, prostate cancer, pancreatic cancer, melanoma, bladder cancer, kidney cancer, head and neck cancer, colorectal cancer, liver cancer, ovarian cancer, neuroblastoma, sarcoma, osteosarcoma, esophageal, brain & ONS, larynx, bronchus, oral cavity and pharynx, stomach, testis, thyroid, uterine cervix, or uterine corpus cancer. The cancer may be a solid tumor, such as solid tumor of a stage I, stage II, stage III, or stage IV cancer. The solid tumor may be a carcinoma, sarcoma, neuroblastoma or melanoma. Examples of lung cancer include, but are not limited to, non-small cell lung carcinoma (NSCLC).

In certain of the relevant embodiments and aspects defined above, at least one CTC, EMTCTC, CAML, or CAVE exhibits at least one RAD50 foci.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF DRAWINGS

The patent or application file contains at least one drawing executed in color. Copies of this patent or patent application publication with color drawing(s) will be provided by the Office upon request and payment of the necessary fee.

(FIG. 1A) An example of a EMTCTC cluster of cells, weakly positive for cytokeratin, negative for EpCAM and negative for CD45. Box scale=90 µm. (FIG. 1B) The samples is quenched by QUAS-R where the fluors are quenched without harming the protein epitopes[13]. The samples are then restained with PD-L1, RAD50 and PD-1. Box scale=90 µm. (FIG. 1C) PD-L1 is measured by tracing the cell in Zen software which calculated the average intensity of each cell or cell cluster. Box scale=35 µm. (FIG. 1D) RAD50 foci (red) are enumerated in each nucleus (Cyan). Box scale=35 µm.

(FIG. 2A) PDCTC with a filamentous cytokeratin signal, pathologically aberrant nuclei and no CD45. White arrow shows a typical white blood cells positive for DAPI and CD45. (FIG. 2B) EMTCTC with a diffuse cytokeratin signal, no CD45 and abnormal nuclei. (FIG. 2C) CAML with multiple aggregated nuclei and an enlarged cell that is both $CD45^+$ and $cytokeratin^+$. Boxes=65 µm.

(FIG. 4A) Clone 22c3 from patient ID #8 sample which scored 1+ in 10% of the tumor. (FIG. 4B) Clone 28-8 from patient ID #8 parallel sample which scored 2+ in 20% of the tumor. (FIG. 4C) A PD-L1 clone optimized for BBBs was used to determine the number of cells positive for PD-L1 and the intensity of each cell found on the CellSieve™ microfilters. SI=pixel intensity quartile, %=percent of cells positive for the maximum pixel intensity quartile, N/A=no available sample to test.

(FIG. 6A) Formation of RAD50 foci can be accurately enumerated and a clear increase in RAD50 loci was observed after the induction of radiotherapy. This suggests that both EMTCTC and CAMLs are originating from the site of radiation. (FIG. 6B) PD-L1 can be evaluated in both EMTCTCs and CAMLs originating from the primary tumor site. Error bars=standard error.

(FIGS. 7A and 7B) In the CAML cells an increase in RAD50 was seen in 59% of patients, 15% of patients had no change and 27% patients didn't have CAMLs at one of the time points. In the EMTCTCs an increase in RAD50 was seen in 44% of patients, 2% of patients had no change, and 54% of patients didn't have EMTCTCs at one of the time points. (FIGS. 7C and 7D) In CAML cells an average PD-L1 increase was seen in 51% of patients, a decrease was seen in 22%, and 27% patients didn't have CAMLs at one of the time points. In EMTCTCs an average PD-L1 increase was seen in 29% of patients, a decrease was seen in 17% and 54% patients didn't have EMTCTCs at one of the time points.

(FIG. 8A) PFS of patients with high PD-L1 expression (2-3 BBB IHC) versus patients with low PD-L1 expression (0-1 BBB IHC) at T0, median PFS 16 vs >24 months. (FIG. 8B) PFS of patients with high PD-L1 expression versus patients with low PD-L1 expression at T1, median PFS 16 vs 18 months, p=0.958. (FIG. 8C) PFS of patients averaging ≤1 RAD50 loci per circulating cell at T0, median PFS 19 vs 18 months, p=0.246. (FIG. 8D) PFS of patients averaging ≤1 RAD50 loci per circulating cell at T1, median PFS 10 vs 19 months, p=0.034.

FIG. 9A—top of cluster imaged through FIG. 9G. Bottom of cluster. All RAD50 foci can be found localized to within the nuclear structure verifying that the RAD50 foci are a nuclear specific component.

(FIG. 16A) PD-L1 staining before treatment with pembrolizumab. (FIG. 16B) PD-L1 staining after treatment for one month with pembrolizumab.

DETAILED DESCRIPTION OF THE INVENTION

I. Definitions

Figure 1:
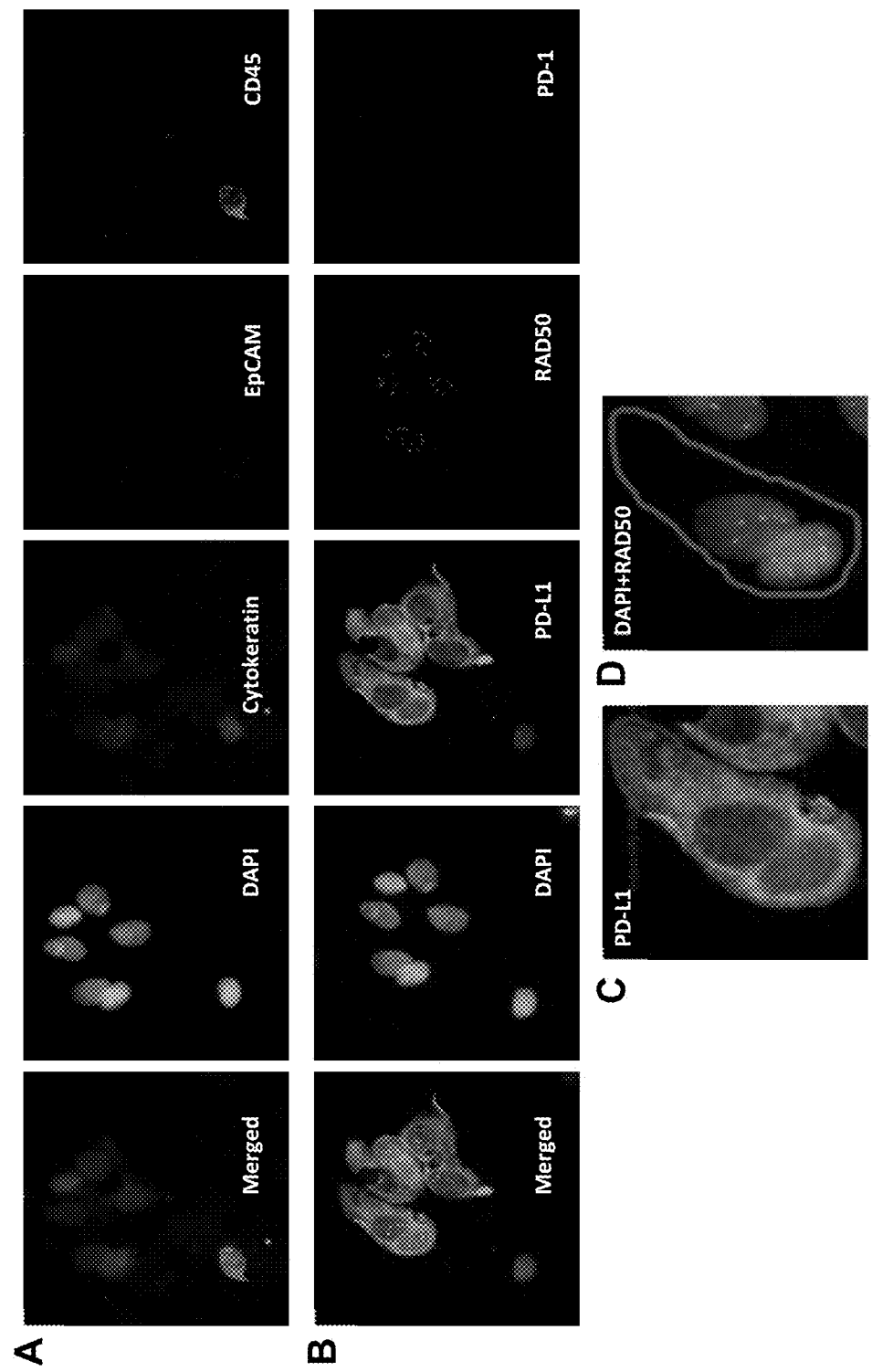
FIG. 1. Blood based biopsy identifies and subtypes circulating cells by DAPI, cytokeratin, EpCAM and CD45; then the QUAS-R fluorescence quenching technique is used to restain cells with RAD50 and PD-L1.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

II. The Present Invention

Liquid biopsies provide real-time, sequential tracking of circulating tumor cells (CTCs) found in the peripheral blood and such assays can be used as a substitute to tissue biopsies[1-4]. Assessing circulating tumor cells (CTCs) in the peripheral blood has the power to interrogate heterogeneous populations of CTCs, including CTC subtypes undergoing epithelial to mesenchymal transition (EMTCTCs)[2, 3, 5-9] and the prognostically relevant pathologically definable CTCs (PDCTCs)[6-10], both as a cancer diagnostic as well as a means for screening, monitoring treatment, and determining the susceptibility of a tumor in a particular subject to a particular treatment.

Recently, another circulating cell associated with cancer has been identified in the peripheral blood of cancer patients that may be assayed in the methods defined herein. This cancer stromal cell subtype has been termed a cancer associated macrophage-like cell or CAML. CAMLs have been identified in the blood using a non-affinity microfiltration based method which captures both CTCs and CAMLs, and allows for singular or parallel analysis of these cancer specific circulating cell subtypes[1, 6-16]. CAMLs are a recently defined circulating myeloid derived stromal cell, found in all the stages of invasive malignancy and in various solid malignancies (e.g. breast, prostate, non-small cell lung carcinoma (NSCLC), and pancreatic)[11, 13, 14, 17]. CAMLs are specialized myeloid polyploid cells in the blood in all stages of solid tumors. They are easy to identify by their large size (greater than 25 μm), polyploid nucleus and morphologies: round, rod shaped, with one tail or two tails 180 degrees apart. CAMLs typically express CD31, CD14, CD45 and cytokeratin, and can also express EpCAM, CD146, CD11c and tie2[11, 13, 14, 17]. While CAMLs appear to be cancer specific and disseminate from the organ sites of malignancy, it remains unknown if they actually reside at the primary tumor site or if they possess clinical utility.

Different subgroups of CTCs upregulate and/or down regulate phenotypes in relation to tumor progression, tumor spread, and in response to tumor treatments. The ability of individual cancer cells to transition states, such as the epithelial to mesenchymal transitions, leads to an additional circulating cancer cell subtype that may be assayed in the methods defined herein, namely epithelial to mesenchymal transition CTCs (EMTCTCs). EMT is a gradual morphogenetic process, and EMTCTCs encompass cells in various stages of transition[6]. EMTCTCs can be generally described by the down regulation of epithelial proteins, e.g. EpCAM and CK, and the upregulation of mesenchymal stem cell proteins, e.g. vimentin and CD34[13]. EMTCTC subtyping is typically performed using non-proteomic methods, i.e. mRNA expression or DNA analysis[13].

A further circulating cell type associated with cancer that may be assayed in the methods defined herein is the cancer-associated vascular endothelial cell or CAVE. CAVEs are a subtype of circulating endothelial cells. Tumors require blood supply provided by tumor endothelial cells. CAVES are tumor endothelial cells that have broken off from the tumor site into the blood stream. CAVEs are often found in clusters. CAVEs express cytokeratin and various subtypes endothelial cell markers such as CD31, CD146, CD144, CD105, but do not express CD14 or CD45[50].

The utilization of such circulating cells has not been well studied in liquid biopsies and the present invention is directed to methods of using CTCs, CAMLs, CAVEs and EMTCTCs in the screening, monitoring, diagnosis and treatment of different cancers, in particular those cancers in which associated CTCs, CAMLs, CAVEs and EMTCTCs express PD-L1 on their surface.

Methods of Screen for Susceptibility to Immune Checkpoint Inhibitor

As indicated above, the present invention is directed to methods of screening a subject having cancer for susceptibility to an immune checkpoint inhibitor. The method comprises assaying one or more of circulating tumor cells (CTCs), epithelial to mesenchymal transition CTCs (EMTCTCs), cancer associated macrophage-like cells (CAMLs), and cancer associated vascular endothelial cells (CAVEs) isolated from a subject having cancer for PD-L1 expression, wherein when PD-L1 expression is detected, the subject is deemed susceptible to an immune checkpoint inhibitor.

Methods of Predicting Responsiveness to Immune Checkpoint Inhibitor

The invention is also drawn to methods of predicting responsiveness of a subject having cancer to treatment with an immune checkpoint inhibitor. The method comprises assaying one or more of CTCs, EMTCTCs, CAMLs, and CAVEs isolated from a subject having cancer for PD-L1 expression, wherein when PD-L1 expression is detected, the subject is predicted to be responsive to treatment with an immune checkpoint inhibitor.

Methods for Selecting Immune Checkpoint Inhibitor Treatments

In addition, the invention is drawn to methods for selecting a treatment for a subject having cancer. The method comprises assaying one or more of CTCs, EMTCTCs, CAMLs, and CAVEs isolated from a subject having cancer for PD-L1 expression, wherein when PD-L1 expression is detected, administration of a therapeutically effective amount of an immune checkpoint inhibitor to the subject is selected as a treatment for the subject.

Assays for Identifying Subject for Immune Checkpoint Inhibitor Treatment

Moreover, the invention is drawn to assays for identifying a subject having cancer to receive an immune checkpoint inhibitor treatment. The method comprises assaying one or more of CTCs, EMTCTCs, CAMLs, and CAVEs isolated from a subject having cancer for PD-L1 expression, wherein when PD-L1 expression is detected, the subject is identified as a subject to receive an immune checkpoint inhibitor treatment.

Methods of Treatment Using Immune Checkpoint Inhibitors

The invention is also drawn to methods of treating a subject having cancer. The method comprises (a) assaying one or more of CTCs, EMTCTCs, CAMLs, and CAVEs isolated from a subject having cancer for PD-L1 expression, and (b) administering a therapeutically effective amount of an immune checkpoint inhibitor to the subject when PD-L1 expression is detected. The immune checkpoint inhibitor may be administered as a pharmaceutical formulation comprising the immune checkpoint inhibitor and a pharmaceutically acceptable carrier.

In a related embodiment, the invention is drawn to methods of treating a subject having cancer. The method comprises administering a therapeutically effective amount of an immune checkpoint inhibitor to a subject having cancer, wherein said immune checkpoint inhibitor is administered after PD-L1 expression is detected in one or more of CTCs, EMTCTCs, CAMLs, and CAVEs isolated from the subject having cancer. The immune checkpoint inhibitor may be administered as a pharmaceutical formulation comprising the immune checkpoint inhibitor and a pharmaceutically acceptable carrier.

In each of the embodiments and aspects of the invention related to methods of treatment, the methods can be practiced using immune checkpoint inhibitors alone or practiced in conjunction with additional means for treating and inhibiting cancer in a subject (e.g., the additional anti-cancer agents defined herein). Such additional means will be well known to the skilled artisan and include, but are not limited to means such as anti-cancer chemotherapeutics and radiotherapeutics and surgical removal of a tumor.

As used herein, the terms "treat", "treating" and "treatment" have their ordinary and customary meanings, and include one or more of complete or partial clearance of a tumor or cancer from a subject, reducing the size of a tumor in a subject, killing cells of a tumor or cancer in a subject, and ameliorating a symptom of cancer or a tumor in a subject. Treatment means clearing, reducing, killing or ameliorating by about 1% to about 100% versus a subject to which an immune checkpoint inhibitor has not been administered. Preferably, the clearing, reducing, killing or ameliorating is about 100%, about 99%, about 98%, about 97%, about 96%, about 95%, about 90%, about 80%, about 70%, about 60%, about 50%, about 40%, about 30%, about 20%, about 10%, about 5% or about 1%. The results of the treatment may be permanent or may continue for a period of days (such as 1, 2, 3, 4, 5, 6 or 7 days), weeks (such as 1, 2, 3 or 4 weeks), months (such as 1, 2, 3, 4, 5, 6 or more months) or years (such as 1, 2, 3, 4, 5, 6 or more years).

As used herein, the terms "inhibit", "inhibiting" and "inhibition" have their ordinary and customary meanings, and include one or more of, hindering, impeding, obstructing, deterring or restraining establishment of cancer or a tumor, development of cancer or a tumor, growth of cancer or a tumor and metastasis. Inhibition means hindering by about 1% to about 100% versus a subject to which an immune checkpoint inhibitor has not been administered. Preferably, the hindering is about 100%, about 99%, about 98%, about 97%, about 96%, about 95%, about 90%, about 80%, about 70%, about 60%, about 50%, about 40%, about 30%, about 20%, about 10%, about 5% or about 1%. The methods of inhibition may be practiced in a subject prior to, concurrent with, or after the onset of clinical symptoms of cancer or a tumor. Thus, the subject may have cancer or a tumor, or merely be susceptible to developing cancer or a tumor. The results of the inhibition may be permanent or may continue for a period of days (such as 1, 2, 3, 4, 5, 6 or 7 days), weeks (such as 1, 2, 3 or 4 weeks), months (such as 1, 2, 3, 4, 5, 6 or more months) or years (such as 1, 2, 3, 4, 5, 6 or more years).

The immune checkpoint inhibitors and pharmaceutical formulations comprising immune checkpoint inhibitors may be administered to a subject using different schedules, depending on the particular aim or goal of the method; the age and size of the subject; and the general health of the subject, to name only a few factors to be considered. In general, the immune checkpoint inhibitors and pharmaceutical formulations may be administered once, or twice, three times, four times, five times, six times or more, over a course of treatment or inhibition. The timing between each dose in a dosing schedule may range between days, weeks, months, or years, an includes administered once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more weeks. The same quantity of immune checkpoint inhibitor may be administered in each dose of the dosing schedule, or the amounts in each dose may vary. The identity of the immune checkpoint inhibitor may also vary or remain the same in each dose in a dosing schedule.

In each of the methods of the present invention, a "therapeutically effective amount" of an immune checkpoint inhibitor or pharmaceutical formulation comprising an immune checkpoint inhibitor is administered to a subject. The therapeutically effective amount will vary between subjects. However, the therapeutically effective amount is one that is sufficient to achieve the aim or goal of the method, whether inhibiting or treating. As an example, a therapeutically effective amount of an immune checkpoint inhibitor used in the methods of the invention is typically between about 0.1 µg to about 10,000 µg of immune checkpoint inhibitor per kg of body weight of the subject to which the peptide is administered. A therapeutically effective amount also includes between about 0.5 µg to about 5000 µg, between about 1 µg to about 500 µg, between about 10 µg to about 200 µg, between about 1 µg to about 800 µg, between about 10 µg to about 1000 µg, between about 50 µg to about 5000 µg, between about 50 to about 500 µg, between about 100 µg to about 1000 µg, between about 250 µg to about 2500 µg, between about 500 µg to about 2000 µg, between about 10 µg to about 800 µg, between about 10 µg to about 1000 µg, between about 1 µg to about 300 µg, and between about 10 µg to about 300 µg of immune checkpoint inhibitor per kg of body weight of the subject.

Appropriate doses and dosing schedules can readily be determined by techniques well known to those of ordinary skill in the art without undue experimentation. Such a determination will be based, in part, on the tolerability and efficacy of a particular dose.

Administration of the immune checkpoint inhibitor or pharmaceutical formulation may be via any of the means commonly known in the art of peptide delivery. Such routes include intravenous, intraperitoneal, intramuscular, subcutaneous and intradermal routes of administration, as well as nasal application, by inhalation, ophthalmically, orally, rectally, vaginally, or by any other mode that results in the immune checkpoint inhibitor or pharmaceutical formulation contacting mucosal tissues.

The pharmaceutical formulations of the invention comprise one or more immune checkpoint inhibitors and a pharmaceutically acceptable carrier. Suitable examples of carriers are well known to those skilled in the art and include water, water-for-injection, saline, buffered saline, dextrose, glycerol, ethanol, propylene glycol, polysorbate 80 (Tween-80™), poly(ethylene)glycol 300 and 400 (PEG 300 and 400), PEGylated castor oil (e.g. Cremophor EL), poloxamer 407 and 188, hydrophilic and hydrophobic carriers, and combinations thereof. Hydrophobic carriers include, for example, fat emulsions, lipids, PEGylated phospholipids, polymer matrices, biocompatible polymers, liposperes, vesicles, particles, and liposomes. The terms specifically exclude cell culture medium. The formulations may further comprise stabilizing agents, buffers, antioxidants and preservatives, tonicity agents, bulking agents, emulsifiers, suspending or viscosity agents, inert diluents, fillers, and combinations thereof.

A kit comprising the necessary components for practicing the methods disclosed herein is also within the purview of the present invention. The kit comprises one or more immune checkpoint inhibitors and instructions for use. In some aspects, the one or more immune checkpoint inhibitors are in a pharmaceutical formulation comprising the immune checkpoint inhibitors and a pharmaceutically acceptable carrier.

Methods of Monitoring PD-L1 Expression

The invention also encompasses methods of monitoring PD-L1 expression in a subject having cancer. The method comprises (a) assaying one or more of CTCs, EMTCTCs, CAMLs, and CAVEs isolated at a first time point from a subject having cancer for PD-L1 expression, (b) assaying one or more of CTCs, EMTCTCs, CAMLs, and CAVEs isolated at a second time point from a subject having cancer for PD-L1 expression, and (c) comparing PD-L1 expression assayed in the cells isolated at the first and the second time points. In particular aspects of this embodiment, the subject is undergoing treatment for cancer.

Methods of Monitoring Treatment

The invention further encompasses methods of monitoring treatment in a subject having cancer. The method comprises (a) assaying one or more of CTCs, EMTCTCs, CAMLs, and CAVEs isolated at a first time point from a subject undergoing treatment for cancer for PD-L1 expression, (b) assaying one or more of CTCs, EMTCTCs, CAMLs, and CAVEs isolated at a second time point from a subject undergoing treatment for cancer for PD-L1 expression, and (c) comparing PD-L1 expression assayed in the cells isolated at the first and the second time points, thereby monitoring treatment in a subject having cancer. In particular aspects of this embodiment, the subject is being treated using an immune checkpoint inhibitor.

Immune Checkpoint Inhibitors

As used herein, the term "immune checkpoint inhibitor" refers to a compound, such as a drug (including an antibody), that inhibits or blocks proteins expressed by cells of the immune system, such as T cells, and some types of cancer cells. These proteins inhibit immune responses and they can block T cells from killing cancer cells. When these proteins are blocked, inhibition of the immune system is overcome and T cells are able to kill cancer cells. Examples of checkpoint proteins found on T cells or cancer cells include PD-1/PD-L1 and CTLA-4/B7-1/B7-2. Immune checkpoint inhibitors thus seek to overcome one of cancer's main defenses (i.e., T cells) against an immune system attack.

The immune checkpoint inhibitors of present invention include, but are not limited to, PD-L1 antagonists, PD-1 antagonists, and CTLA-4 antagonists.

The immune checkpoint inhibitors of present invention also include, but are not limited to, inhibitors one or more of (i) binding between PD-L1 and PD-1, (ii) binding of PD-L1 to its binding partner(s), (iii) binding of PD-1 to its binding partner(s), and (iv) binding of CTLA-4 to its binding partner(s).

The immune checkpoint inhibitors of present invention further include, but are not limited to, antibodies, such as monoclonal antibodies. In particular aspects, the immune checkpoint inhibitor is a human antibody, a humanized antibody, or a chimeric antibody. The immune checkpoint inhibitors also include fragments of antibodies that retain their inhibitory activity. Such antibody fragments include, but are not limited to, Fab fragments, F(ab')2 fragments, and single chain Fv (scFv). In one aspect, the immune checkpoint inhibitor is an antibody having binding specificity for PD-L1, PD-1 or CTLA-4, or antibody fragment thereof.

Examples of specific immune checkpoint inhibitors include, but are not limited to, one or more of Nivolumab (Opdivo), Ipilimumab (Yervoy), Pembrolizumab (Keytruda), Atezolizumab (Tecentriq), Tremelimumab, and Durvalumab (MED14736).

Anti-Cancer Agents

In the embodiments and aspects of the invention directed to the treatment of cancer, the methods may include the administration of a therapeutically effective amount of one or more anti-cancer agents to the subject in addition to the immune checkpoint inhibitors.

The anti-cancer agents are only limited in that they be compatible with the immune checkpoint inhibitors that are also administered to the subject.

Additional anti-cancer agents include, but are not limited to, immunotherapeutic agents, chemotherapeutic agents, radiotherapeutic agents, existing cancer drugs, CCR5 and CXCR4. Examples of specific anti-cancer agents include, but are not limited to, one or more of T-VEC, AM-0010, CXCR4 antagonist, TGF-beta kinase inhibitor galunisertib, anti-CSF-1R monoclonal antibody, Abemaciclib, Faslodex, necitumumab, AZD9291, Cyramza (ramucirumab), TPIV 200, Galunisertib, cancer vaccines, cytokines, cell-based therapies, bi- and multi-specific antibodies, tumor-targeting mAbs, Rituximab, oncolytic viruses, reovirus, Blinatumomab, Sipuleucel-T, T-Vec, IL-2, IFN-α, Trastuzumab, Celuximab, bevacizumab, Tim-3, BTLA, anti-IL-10, GM-CSF, anti-angiogenesis treatment, VEGF blockade, HMGB1, Nrp1, TAM receptor tyrosine kinases, Axl, MerTK, ALT-803, IL-15, Immunosuppressive Ligand Phosphatidylserine (PS), bavituximab, bevacizumab (anti-VEGF), coblmetinib (MEK inhibitor), vemurafenib (BRAF inhibitor), erlotinib (EGFR), alectinib (ALK inhibitor), bevacizumab (anti-VEGF), pazopanib (tyrosine kinase inhibitor), dabrafenib (BRAF inhibitor), trametinib (MEK inhibitor), durvalumab (anti-PD-L1), sunitinib (RTK inhibitor), pazopanib (RTK inhibitor), sargramostim, VISTA, TIM-3, LAG-3, PRS-343, CD137 (4-1BB)/HER2 bispecific, USP7, anti-HER2, SEMA4D, CTLA-4, PD-1, PD-L1, and PD-L2.

Means for Assaying PD-L1 Expression

As will be apparent, the methods of the present invention are based on assaying, i.e. detecting and/or measuring PD-L1 expression in a cell. In one aspect of the invention, each of the methods defined herein can be used by simply determining whether a selected cell expresses PD-L1. Thus, these methods can be performed without the need to quantify the amount of PD-L1 expression in a cell. However, and in another aspect of the invention, each of the methods defined herein can be used by determining the relative or specific amount of PD-L1 expression by a cell. The relative amount may be determined, for example, by determining whether a cell expresses more or less PD-L1 than another cell or standard. The specific amount may be determined, for example, by quantifying the level of PD-L1 expression in a cell.

PD-L1 expression may be assayed by one or more of detecting/measuring PD-L1 protein expression and detecting/measuring PD-L1 mRNA production. PD-L1 protein expression may be detected/measured, for example, via immunohistochemistry (IHC). IHC may be performed by membrane staining, cytoplasmic staining, or a combination thereof. IHC may be performed using an anti-PD-L1 antibody, such as, but not limited to, E1L3N, SP142.2, 28-8, 22C3, EPR19759, MIH2, MIH5, MIH6, ABM4E54, 130021, EPR20529, 10F.9G2, and CD274. PD-L1 protein expression may be detected/measured as a weak staining intensity, moderate staining intensity, or strong staining intensity. PD-L1 protein expression may also be detected as a low staining intensity, moderate staining intensity, or high staining intensity. PD-L1 protein expression may also be detected as inducible from low staining intensity to high staining intensity over time, or inducible from low staining intensity to moderate staining intensity over time, or inducible from moderate staining intensity to high staining intensity over time. PD-L1 protein expression may also be detected/measured simply as any staining whatsoever of the isolated cells, for example—any amount of staining above background.

In certain aspects, IHC is performed using immunofluorescence (IF) staining. One or more antibodies with binding specificity for PD-L1 may be utilized to detected PD-L1 protein expression. Binding of the anti-PD-L1 antibody to PD-L1 may be detected via a fluorescent compound or other detectable label conjugated to the anti-PD-L1 antibody or it may be detected via a fluorophore or other detectable label conjugated to a secondary antibody that, in turn, has binding specificity for the anti-PD-L1 antibody.

In certain of the relevant embodiments and aspects defined above, PD-L1 expression is determined to be detected when the level of PD-L1 expression is greater than PD-L1 expression is a population of stromal cells from a subject of the same species that does not have cancer.

Source of Cells

The cells used in the methods of the present invention include one or more of CTCs, EMTCTCs, CAMLs, and CAVEs. Thus, the methods may be performed using one, two, three or all four of these types of circulating cells.

The cells may be obtained from any bodily fluid in which the cells can be found, including blood, such as peripheral blood. Blood samples may be collected in CellSave Preservative Tubes™ for example, and the blood may be processed with a CellSieve™ Microfiltration Assay using a low-pressure vacuum system, for example.

Subjects

The subjects mentioned in the methods of the present invention will be a human, a non-human primate, bird, horse, cow, goat, sheep, a companion animal, such as a dog, cat or rodent, or other mammal.

The subject having cancer may be undergoing treatment for the cancer. Such treatments include, but are not limited to targeted agents, chemotherapy, and radiation therapy. The cancer may be one or more of lung cancer, breast cancer, prostate cancer, pancreatic cancer, melanoma, bladder cancer, kidney cancer, head and neck cancer, colorectal cancer, liver cancer, ovarian cancer, neuroblastoma, sarcoma, osteosarcoma, esophageal, brain & ONS, larynx, bronchus, oral cavity and pharynx, stomach, testis, thyroid, uterine cervix, or uterine corpus cancer. The cancer may be a solid tumor, such as solid tumor of a stage I, stage II, stage III or stage IV cancer. The solid tumor may be, but is not limited to, carcinoma, sarcoma, neuroblastoma or melanoma. Example of lung cancers include, but are not limited to, non-small cell lung carcinoma (NSCLC).

RAD50 Foci

In certain of the relevant embodiments and aspects defined above, at least one CTC, EMTCTC, CAML, or CAVE exhibits at least one RAD50 foci.

Cells originating from tumors receiving site directed radiation are marked by ionizing radiation induced DNA damage, including tumor and stromal cells[18-24]. Thus, circulating cells that originate at the tumor site during radiation therapy should have evidence of DNA damage, such as ionizing radiation induced foci (IRIF) which can be visualized with RAD50[18-24]. RAD50 is a protein that complexes with the proteins NBS1 and MRE11 and is crucial in the DNA double strand repair process following treatment with radiation and/or chemical agents. In normal mammalian cells, RAD50 is distributed throughout both the cytoplasm and the nucleus. Following double stranded breaks in DNA, the RAD50/NBS/MRE11 complex rapidly translocates to the sites of the breakage forming aggregated nuclear foci until the break is repaired, e.g. IRIF[18, 20, 23, 25]. Thus, RAD50 can be used as a specific identifier of cells which have been exposed to high levels of radiation—acting as a biological tag of cells from patients that have been directly exposed to radiation targeted to a tumor mass[18-24, 26-28].

III. Examples

Example 1

Blood Sample Collection

Forty-one patients with stage I-IV lung cancer were included in this prospective pilot study (Table 1). Anonymized peripheral blood samples were collected after written informed consent and according to the local IRB approval. Patients were recruited from July 2013 to May 2014 prior to starting radiotherapy for primary lung cancer. Four patients received Stereotactic Body Radiation Therapy (SBRT) for stage I disease and 37 patients received chemoradiation for stage II-IV disease with proton therapy (n=16) or Intensity-modulated radiation therapy (IMRT) (n=21). Anonymized blood samples (7.5 mL) were drawn and processed on site at the MD Anderson Cancer Center (MDA). Slides were anonymized then shipped and analyzed at Creatv Micro-Tech, Inc.'s clinical core laboratory. Anonymized biopsy samples from primary tumors were processed at MDA according to manufacturer's protocols (DAKO). Results from institutions were not shared or communicated until completion of study.

TABLE 1

Patient population overview

|  |  | Number of patients |
|---|---|---|
| Stage | I | 6 |
|  | II | 6 |
|  | IIIA | 11 |
|  | IIIB | 13 |
|  | IV | 5 |
| Prior Chemotherapy | Yes | 14 |
|  | No | 27 |
| Pathological Grade | 1 | 3 |
|  | 2 | 10 |
|  | 3 | 28 |
| Histology | NSCLC | 31 |
| Squamous cell | NSCLC | 6 |
|  | SCLC | 1 |
|  | unknown | 3 |

CellSieve™ Low-Flow Microfiltration Procedure

Blood samples (7.5 mL) collected in CellSave Preservative Tubes™ were processed with a CellSieve™ Microfiltration Assay using a low-pressure vacuum system[1, 12]. The CellSieve™ Microfiltration Assay isolates circulating cells based on size exclusion, >7 micron. A trained cytologist identified prognostically relevant pathologically definable CTCs (PDCTCs), EMTCTCs and CAMLs based on morphological features and the phenotypic expression of CD45, EpCAM, Cytokeratins 8, 18, 19 and DAPI (FIGS. 1 and 2)[1, 6, 12] using pre-established cytological features described[6, 11, 14]. An Olympus BX54WI Fluorescent microscope with Carl Zeiss AxioCam and Zen2011 Blue (Carl Zeiss) was used for all imaging.

Enumerating PDCTC/EMTCTC Subtypes and CAMLs

The defining characteristics of the two most common CTC subtypes found in cancer patients (PDCTCS and EMTCTCs) and those for CAML identification were previously described[1, 6, 10-14]. For this study only intact PDCTCs, EMTCTCs, and CAMLs were characterized (FIGS. 2 and 3)[1, 6, 10-14] PDCTCs are CD45 negative, with filamentous cytokeratin positivity and DAPI positive nuclei with malignant pathological criteria, classified as the CellSearch® subtype of CTC [1, 6, 10-14]. EMTCTCs are CD45 negative with a diffuse cytokeratin signal and a DAPI positive nucleus with abnormal criteria, as previously defined[1, 6-9, 12, 13]. CAMLs are described as enlarged (>30 µm), multinuclear cells with diffuse cytoplasmic cytokeratin staining, and/or CD45+/CD14+[6, 11, 14, 17, 22, 43]. All 3 cell types were identified and imaged by a trained CTC cytologist and confirmed by a pathologist. Apoptotic CTCs and CTCs that could not be cytologically classified as previously described were not included. After identification, cells were imaged and x-y axis of each cell was marked for future analysis. Samples were archived at 4° C. for 1-3 years.

QUAS-R Quenching and Restaining for PD-L1 and RAD50

Figure 2:
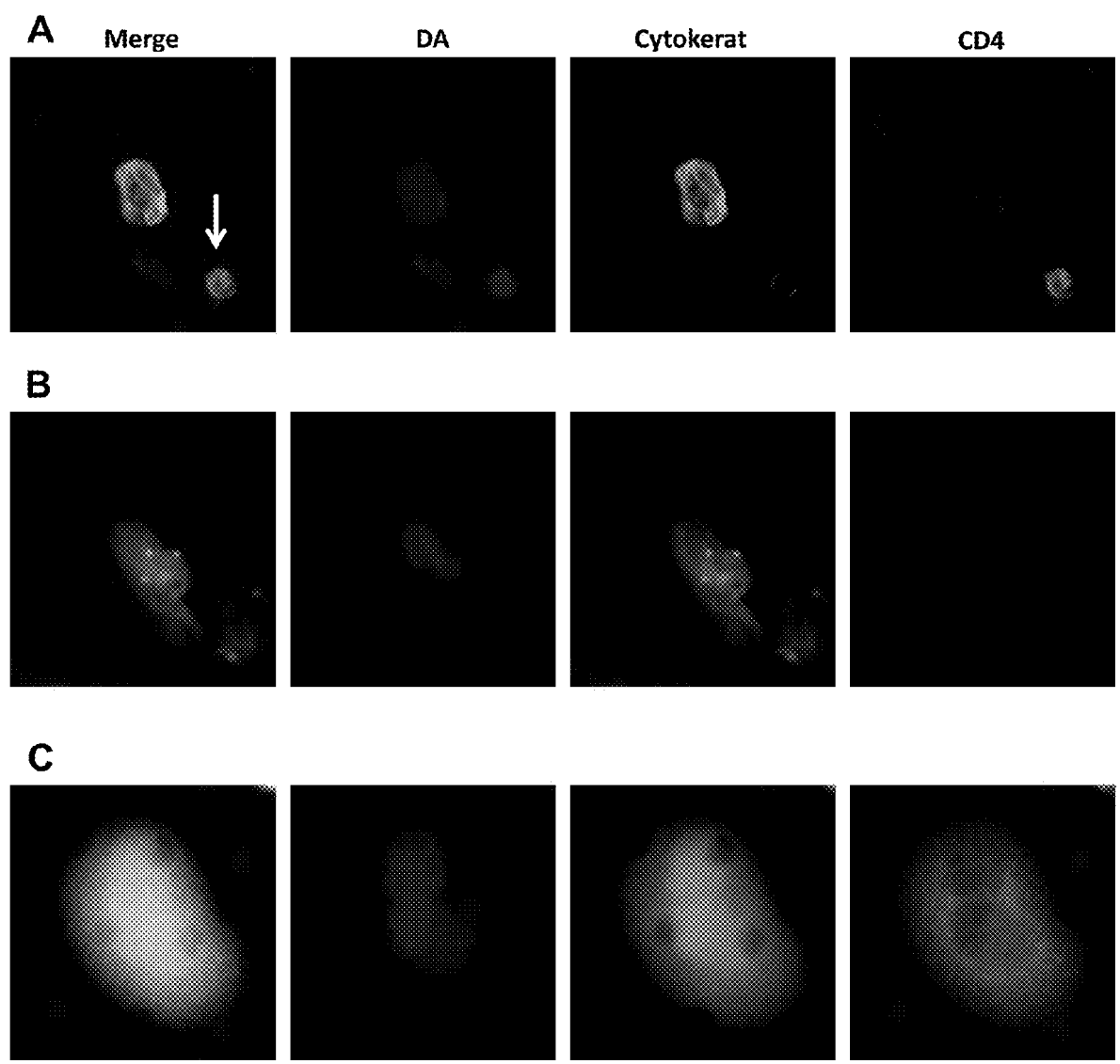
FIG. 2. Individual and expanded images of DAPI, Cytokeratin and CD45 from FIG. 3.

After initial identification and quantification of PDCTCs, EMTCTCs and CAMLs, fluorescence was quenched and samples were restained with RAD50-DyLight 550 (Pierce Thermo), PD-L1-AlexaFluor 488 (R&D systems) and DAPI nuclear stain (FIG. 1). The QUAS-R (Quench, Underivatize, Amine-Strip and Restain) technique was used as previously described[13]. Briefly, after samples were imaged and marked filters were subjected to a sequential chemical treatment of quenching solution, Tris, and wash steps. After chemical quenching, filters were washed with PBS, incubated with 1XPBS/20% FBS and then incubated with antibodies against RAD50-AlexaFluor550 and PD-L1-AlexaFluor 488 for 1 hour at room temp. After antibody incubation, filters are washed in 1×PBST and slide mounted with Fluoromount-G/DAPI (Southern Biotech). Samples were oriented along the x/y axis and previously imaged cells were relocated using a Zen2011 Blue (Carl Zeiss) mark and find software. A Zen2011 Blue (Carl Zeiss) was used to process the images.

Quantifying PD-L1 in Primary Tumor Biopsies

Figure 4:
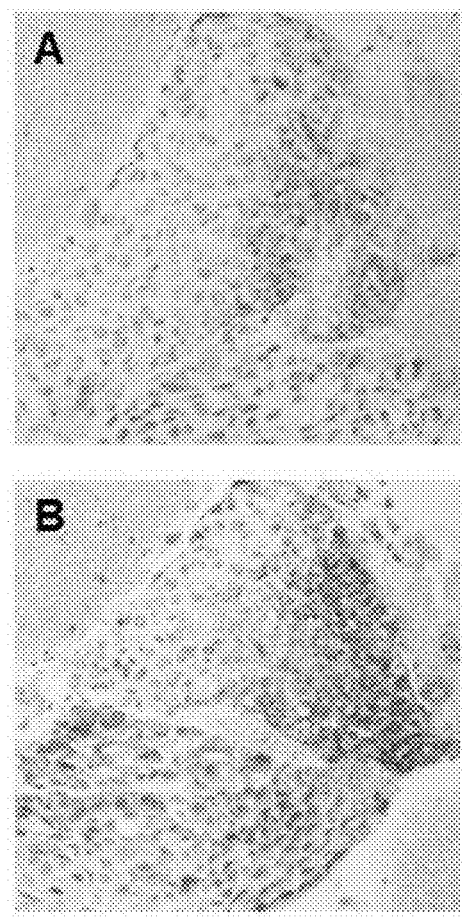
FIG. 4. Testing and comparing the clinically approved IHC PD-L1 clones from DAKO and the BBB PD-L1 clone.

PD-L1 expression from all available primary tumor biopsies were analyzed using both DAKO pharmdx clone 22c3 and DAKO pharmdx clone 28-8 according to manufacturer's guidelines (FIG. 4). Eight patients from the study had sufficient and available archived tumor samples to screen both clones and one sample had sufficient archived tumor for a single IHC test against clone 22c3. Both clones were stained according to standard operating procedures previously described[29-31, 38].

Quantifying RAD50 and PD-L1 in Circulating Cells

Figure 5:
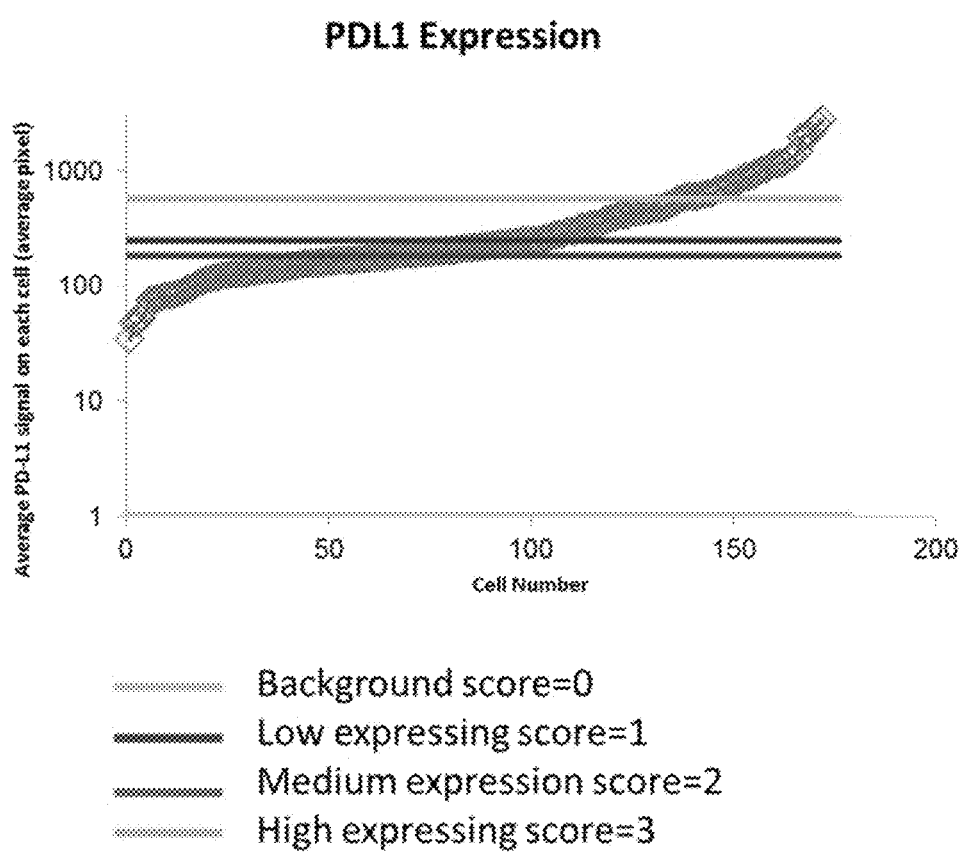
FIG. 5. Determining the thresholds for scoring PD-L1 expression in circulating cells. The PD-L1 signal of each BBB cell (n=374) was determined by Zen Blue and subtracted from it's relative background for each image. The standard deviation of the background (n=373) was used as the threshold for a BBB IHC score of 0 (26% of all cells). Two times the standard deviation was used as the threshold for a BBB IHC score of 1 (42% of all cells). Twice the background was used as the threshold for a BBB IHC score of 2 (22% of all cells). All remaining intensities 2×-6× background were scored as ≥3 (10% of all cells).

RAD50 loci formation was determined by enumerating the nuclear localized RAD50 loci in each cell (FIGS. 1 and 5)[23]. PD-L1 pixel intensity of each cell was measured by the ZenBlue software by using the area of the entire cell. The average pixel intensity of each cell was subtracted from the average pixel intensity of the local background for each image (FIG. 1C). The average pixel intensity of the cells was quartiled into 4 IHC groups: 0-negative (pixel average 0-150), 1-low (pixel average 151-300), 2-medium (pixel average 301-750), and 3-high (pixel average 751+) (FIG. 5). IHC range thresholds of PD-L1 intensity for IHC scoring were determined as: 150 pixel intensity was the standard deviation of the localized background signal, 300 pixel intensity was 2 times the standard deviation of the localized background, and 750 was two times the intensity of the localized background (FIG. 5).

Statistical Methods

Analyses were done in MATLAB R2013A using the counts from all subtypes and the known patient populations. For progression free survival analysis, the time to progression was defined as the interval between when T0 blood sample was obtained to date of progression, all patients remained on study through 24 month end point, i.e. no patients were censored. Significance of the average changes in RAD50 foci formation and PD-L1 expression were determined by a Student's T-test. A Pearson coefficient was used to determine the correlation between RAD50 foci and PD-L1 expression for individual measurements. Significance of Kaplan Meier plots were determined by log-rank analysis.

Results

PDCTCs, EMTCTCs and CAMLs in LC Patients

Figure 3:
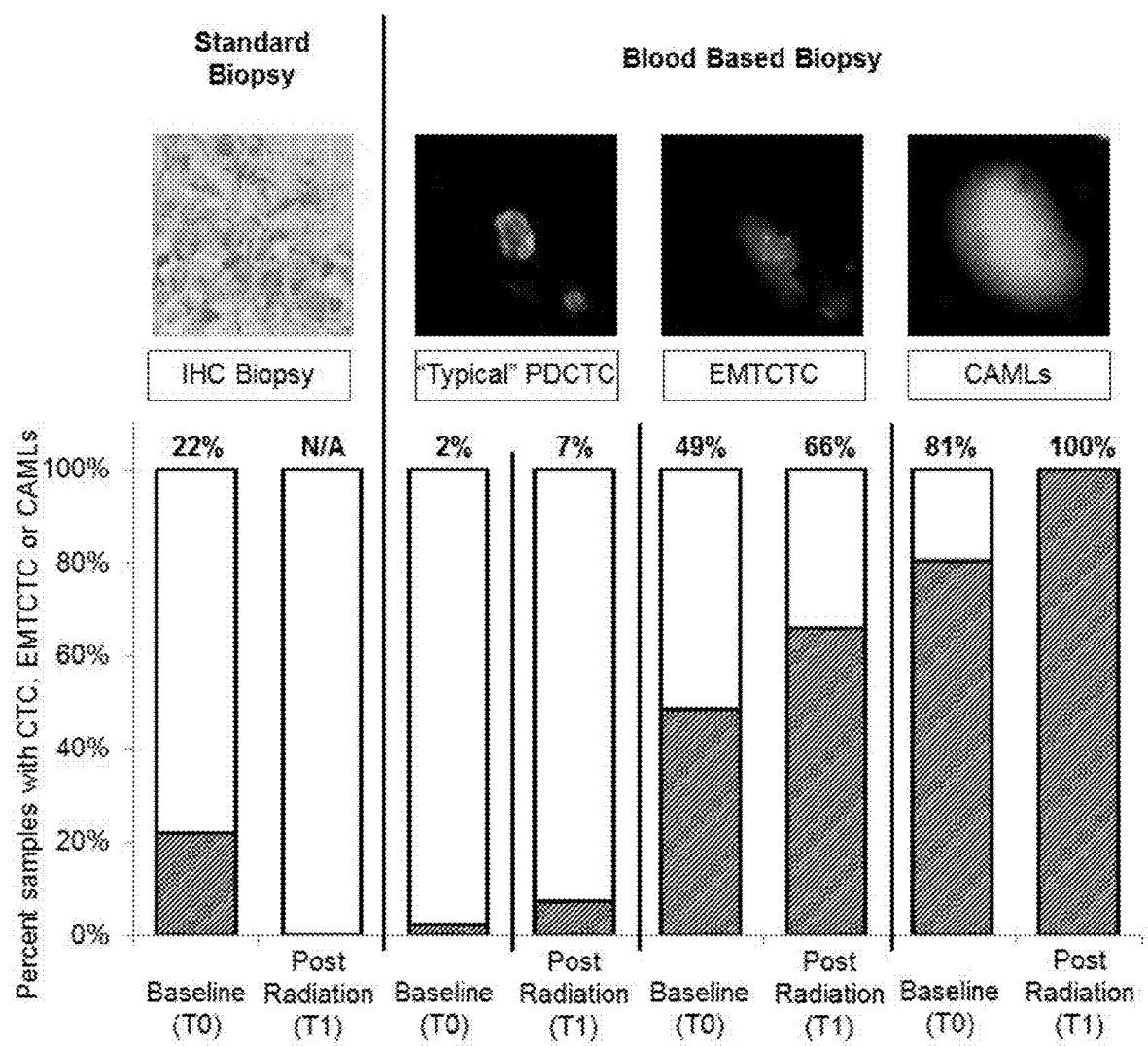
FIG. 3. Percentage of samples with cells that could be used to quantify PD-L1 at baseline (T0) and post induction of radiotherapy (T1), blood based biopsies include two subtypes of circulating tumor cells and circulating stromal cells. Standard biopsies only have the initial baseline time points and only 22% of those samples had sufficient amount of tumor for analysis by PD-L1. Brown stain is PD-L1/blue is hematoxylin. A blood based biopsy identified EMT tumor cells in 49% of baseline samples and in 66% of post therapy samples. Further, circulating stromal cells (CAMLs) were available in 81% of baseline samples and in 100% of follow up samples. Blue=DAPI, green=cytokeratin, purple=CD45, boxes=65 micron.

Prior reports indicated that the CTC subpopulation in NSCLC patients using the CellSearch® platform is typically found in only 0-5% of non-metastatic cases. In contrast, the EMTCTC population is typically found in ~80% of non-metastatic patient populations, while CAMLs have not been extensively evaluated in NSCLC[3-6, 8, 15, 17, 43-45]. In the first baseline blood sample taken prior to start of radiation therapy (T0) we were able to identify at least one cytokeratin positive cell (i.e. PDCTC, EMTCTC or CAML) (FIGS. 1 and 3) in 35 of the 41 samples (85%). Patients then had a second follow up sample (T1) taken 2-3 weeks after radiotherapy initiation or after the last fraction for SBRT patients. For T1, there was at least one cytokeratin positive cell (i.e. PDCTC, EMTCTC or CAML) found in all 41 samples (100%). Specifically, EMTCTCs were found in 49% of T0 samples and in 66% of T1 samples. CAMLs were found in 81% of T0 samples and in 100% of T1 samples (FIG. 3). PDCTCs were found in only 1 sample at T0 (2%) and in only 3 samples at T1 (7%) (FIG. 3). Being that PDCTCs have been shown to be the same CTC population of cells isolated by the CellSearch® CTC System, these numbers are on par with previous reports[7-9, 15]. The CellSearch® system isolates CTCs in NSCLC patients ranging from 0-5% positivity in stage III NSCLC and 21-32% in stage IV[7-9, 15]. As 35 of the patients were staged as I-III, 2-7% is within the range of the classical CTC population (Table 1)[7-9, 15]. The low incidence of the classical PDCTC population (FIG. 3) is in contrast to EMTCTC and CAMLs which are present in 85% (T0) and 100% (T1) of the samples. While it has been postulated that EMTCTCs alone may provide some increased sensitivity for liquid biopsies in NSCLC[7-9, 16], these results suggest that the combination of both EMTCTCs and CAMLs provides improved sensitivity analyzing tumor derived cells for blood based diagnosis.

RAD50 as a Biological Tracker of Irradiated Cells

Figure 6:
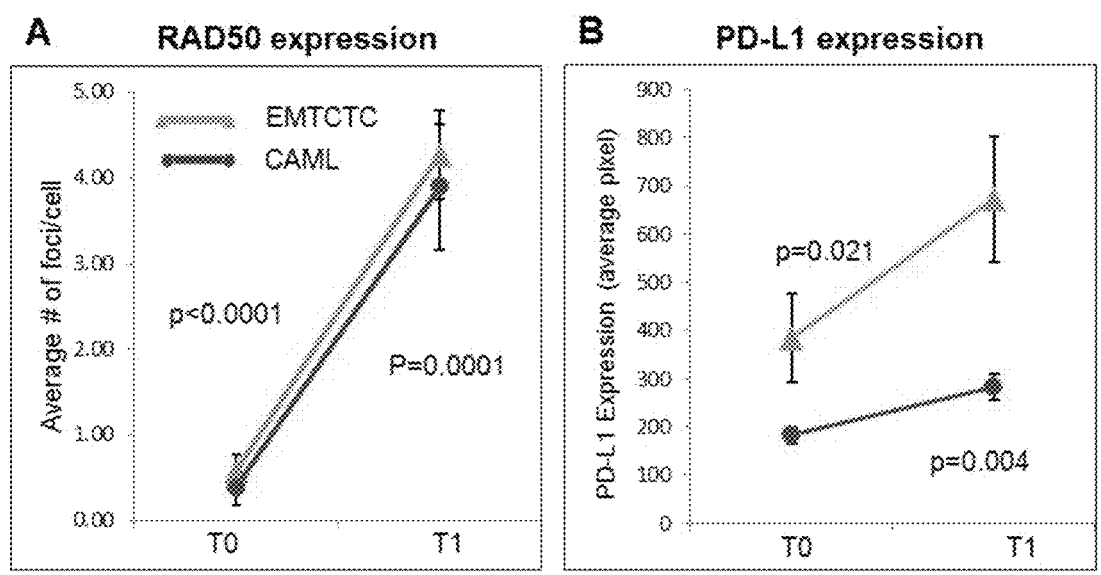
FIG. 6. Dynamic changes in the formation of RAD50 loci within the nucleus and the upregulation of PD-L1 on cells analyzed in both circulating tumor cells and stromal cells throughout treatment using a blood based biopsy approach.
Figure 7:
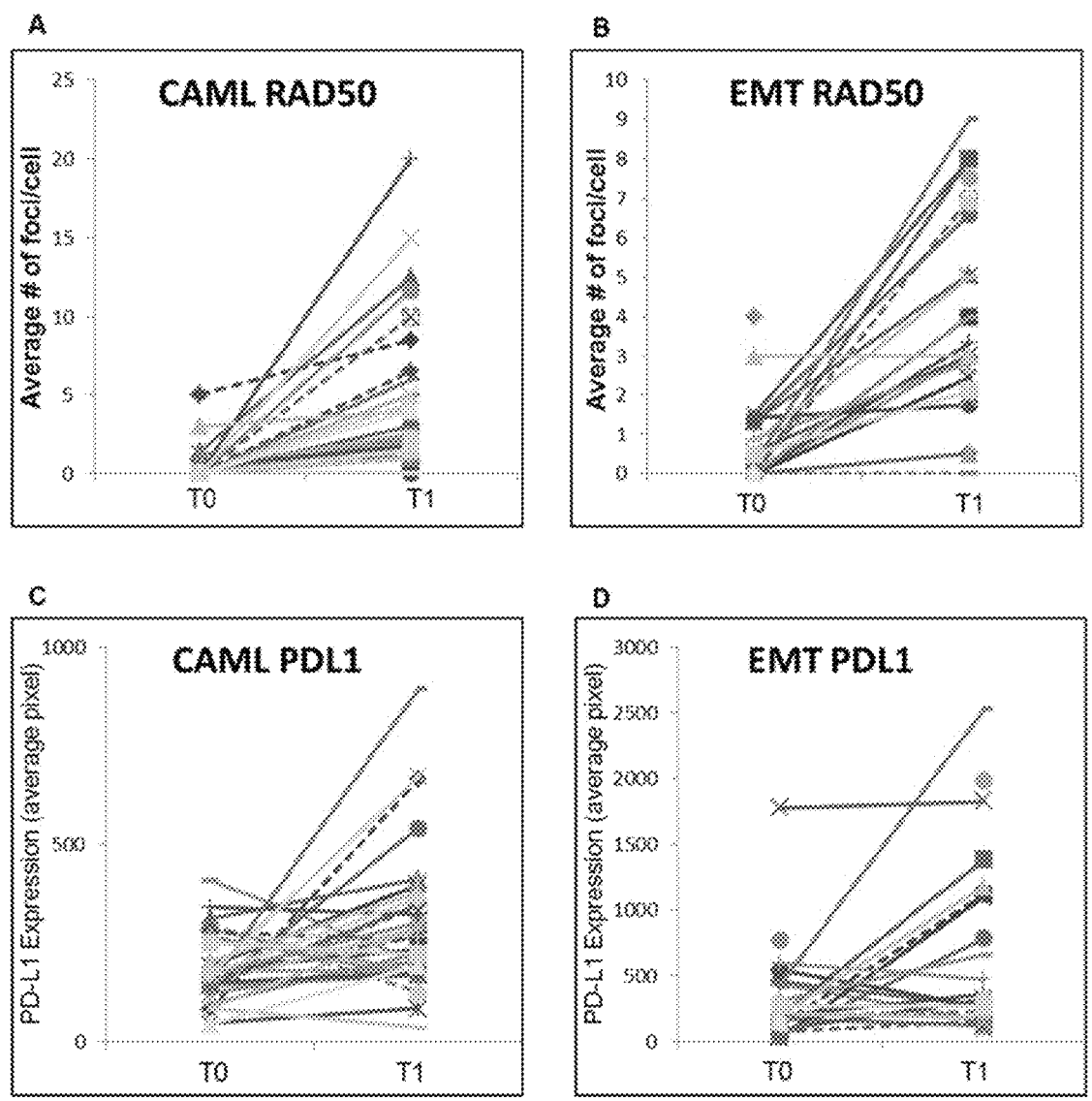
FIG. 7. Average PD-L1 and RAD50 changes in each individual patient before and after induction of radiotherapy, separated by cell type.

While CTCs and CAMLs have been described as disseminating into peripheral blood from the site of a primary tumor, studies have yet to confirm the exact location that these cells reside in prior to entry into circulation. The primary reason for this unknown origin is because labeling tumor/stromal cells in patients and tracking their dissemination is difficult, as such experiments pose a danger to patients. While RAD50 foci within IRIF formations in mammalian cells has been shown as a biological tracker of direct radiation exposure to cells, this has never been evaluated in circulating tumor or stromal cells in patients undergoing radiation. In non-irradiated LC patients at T0 baseline, RAD50 foci in EMTCTCs cells ranged from 0-4 per nuclei with an average of 0.59±0.97 foci and in CAMLs the foci number ranged from 0-5 with an average of 0.38±1.07 (FIGS. 6 and 7). The presence of some RAD50 foci in cells is not surprising as RAD50 foci is a normal biological repair mechanism which is typically identified in a small number of untreated cells[21, 23, 24]. After patients were exposed to tumor-directed radiotherapy at T1, RAD50 foci in EMTCTCs significantly increased to 0-9 per nuclei with an average of 4.27±2.63 and in CAMLs the number increased to 0-20 with an average of 3.9±3.93 per nuclei (FIG. 6). This increase was observed in all patients with detectable cells at both T0 and T1 time points (n=35), and was rarely found in any background of normal CD45+ leukocytes (FIG. 1B).

Thus, RAD50 in both EMTCTCs and CAMLs increased from an average of 0.48 at T0 to an average of 4.05 (p<0.0001) at T1 (FIG. 6). These results suggest that RAD50 may be used to label and track the irradiated cells that originate at tumor sites and thus, can be used to track tumor dynamics.

Dynamic Expression of PD-L1 in Circulating Cells

Figure 8:
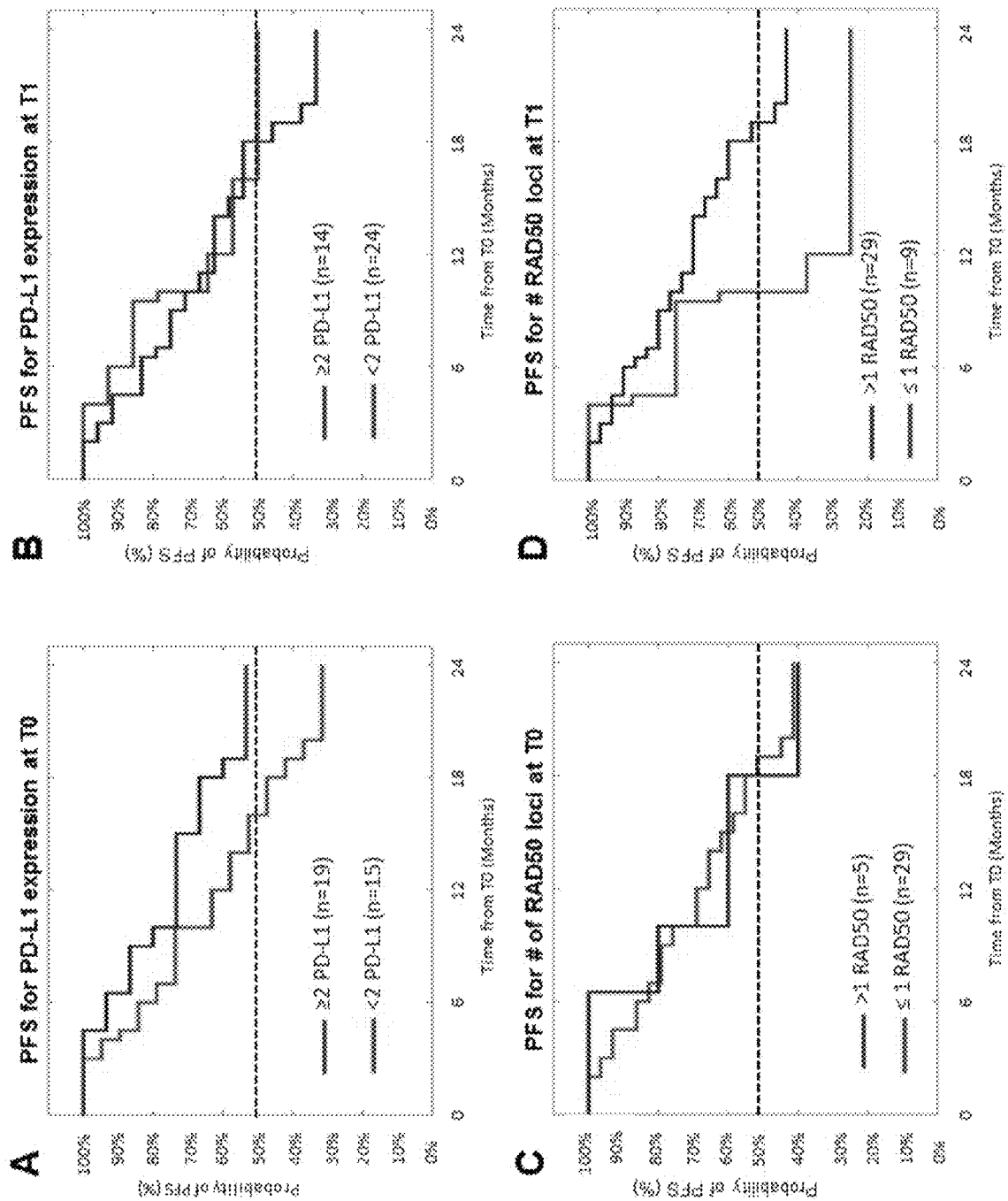
FIG. 8. Comparing the PFS of patients based on high/low PD-L1 expression or RAD50 loci formation pre and post radiotherapy.

There have been suggestions that PD-L1 may be induced in tumors by various cytotoxic therapies, including radiation[29-34, 36-40, 42]. To determine if this could be seen using BBB, we evaluated PD-L1 staining at the T0 and T1 time points. A normalized comparative scoring system was developed in a similar manner to the classical 0-3 IHC tissue biopsy scoring (FIGS. 5 and 8). After staining and imaging, PD-L1 expression and the local background for all 373 cells found in LC patients were measured. The local background of each image averaged 375±150 pixel intensity (FIG. 5). To account for the localized background effect, the background of each image was subtracted from each measured cell, yielding a corrected PD-L1 pixel intensity range of 17-3090 (FIG. 5). We then grouped the cells with the corrected pixel intensities using the standard deviation of background of 0-150 pixels as a score of 0 (26% of cells) and 2 times the standard deviation (151-300 pixels) as a score of 1 (low expression, 42% of cells). Medium expression, a score of 2 (22% of cells) was determined as being 2 times the mean background signal (301-750 pixel) and high expression or score of 3 (10% of cells) was set at >2 times the mean background signal (>750 pixels) (FIG. 5).

Pixel intensity of PD-L1 in EMTCTCs averaged 384±484 at T0 and 672±669 at T1 (p=0.021), while CAMLs had an average of 182±89 at T0 and 282±169 at T1 (p=0.004) (data not shown). Regression analysis found a weak, but significant, positive correlation between RAD50 and PD-L1 from T0 to T1 (Pearson $R^2$=0.079, p<0.0001, n=373). While RAD50 was reliably induced from T0 to T1 among patients, changes in PD-L1 expression in individual patients was far more variable (data not shown). We found 3 distinct patterns of PD-L1 expression between T0 and T1 in the 35 patients who were assessable for both time points. Eighteen patients (51%) had no/low PD-L1 expression at both time points, 6 patients (17%) had persistently medium/high PD-L1 at both time points and 11 patients (32%) saw an increase from a low 0/1 score to a 2/3 score (data not shown).

Comparison of PD-L1 Levels in the Primary Tissue, CTCs and CAMLs

We stained available tissues from the original diagnostic biopsy by IHC using 2 commercially available and CLIA-certified tests using clones 22c3 and 28-8 (DAKO). We were only able to retrieve useable tissue or cell blocks from pathologic archives in 9 of 41 patients, and 1 of these 9 patients only had sufficient tissue for one IHC test (FIG. 4). This was a result of tumor necrosis or small nodules resulting in insufficient mass to perform the PD-L1 IHC testing. Of the 9 archival samples, only 2 had positive PD-L1 staining with some variability in the expression scores and percentages between the 2 tests (FIG. 4C). In comparison, PD-L1 expression was quantifiable in 85% of T0 patient samples (n=35/41) and 100% (n=41/41) in T1 patient samples using the BBB. Specifically at T0, EMTCTCs and CAMLs showed low/negative (score 0/1) PD-L1 expression in 21 patients (60%), medium (score 2) expression in 9 patients (26%) and high (score 3) expression in 5 patients (14%) (FIG. 4C).

At T0, expression of PD-L1 in the circulating cells closely paralleled the IHC biopsy results for 2 IHC positive stained samples using the 28-8 IHC clone results (FIG. 4C). Three patients had concordant negative PD-L1 tissue by IHC and low (0/1) expression on circulating cells, but 3 patients had discordant results with negative tissue IHC PD-L1 but 2/3 scores on the circulating cells, and 1 patient lacked circulating cells in the T0 sample (FIG. 4). Given the limited number of samples, a proper statistical analysis was not possible. However, these results suggest primary biopsies inconsistently provide sufficient tissue for assaying PD-L1 expression while a Blood Based Biopsy (BBB) approach could measure intrinsic levels and monitor changes of PD-L1 expression in circulating cells originating from cell populations found at the primary lung tumor.

PD-L1 and RAD50 in Circulating Cells as Potential Prognostic Markers

In tissue biopsies, expression of the biomarker PD-L1 alone is not a prognostic indicator of survival in lung cancer, while RAD50 foci formation has been indicated as positively correlated with survival[14, 18, 20, 24, 29, 30, 32, 35, 39, 40, 42]. We analyzed the clinical outcomes of patients based on expression of PD-L1, or the average number of RAD50, at both T0 and T1 time points (FIG. 8). For comparing PFS using expression of PD-L1, we used the medium expression as the cut off criteria, i.e. <2 versus ≥2 for the 2 cohorts. Patients with lower PD-L1 at T0 had a slightly worse hazard ratio (HR) of 1.8, which was not significant (p=0.305). At T1, patients with lower PD-L1 had a slightly better overall PFS (HR=0.7), which was also not significant (p=0.581). This data suggests limited to no correlation with overall PFS based on expression of PD-L1 levels at T0 or T1. Using median PFS, we did find a slight trend to better median PFS at T0 in cells with higher PD-L1 (16 months vs >24 months) but confirmation of this requires a much larger sample size.

Because RAD50 foci formation in tissue biopsies has been shown to be positively correlated with survival[18, 20, 24, 26], we assessed its prognostic value in circulating cells (FIG. 8). The number of RAD50 foci in EMTCTCs and CAMLs at T0 had no clinical difference in overall PFS (HR=1.0, p=0.775). However, patients with higher RAD50 foci at T1 did non-significantly trend to better overall PFS (HR 2.3, p=0.27) (FIG. 8). Thus, while overall PFS was not significantly different, the median PFS was 1.9× longer in patients with >1 RAD50 foci/cell compared to patients with ≤1 RAD50 foci/cell (9.8 months vs 18.5 months, respectively. This data suggests that a RAD50 increase in circulating cells after radiotherapy may have prognostic value, an observation that will need further validation and larger sample sizes.

As indicated by the results provided in these preceding paragraphs, we prospectively and sequentially tracked PD-L1 levels and RAD50 foci in three circulating blood cell subtypes PDCTCs, EMTCTCs, and CAMLs from 41 lung cancer patients undergoing (chemo) radiotherapy. We phenotyped circulating cells based on radiation induced RAD50 foci formation to quantifiably track clear biological changes in cells emanating from a primary lung tumor mass. Furthermore, tracking these dynamic changes might be used to differentiate patients with tumors that may have become more sensitized to radiation therapy, though larger studies are needed.

Figure 9:
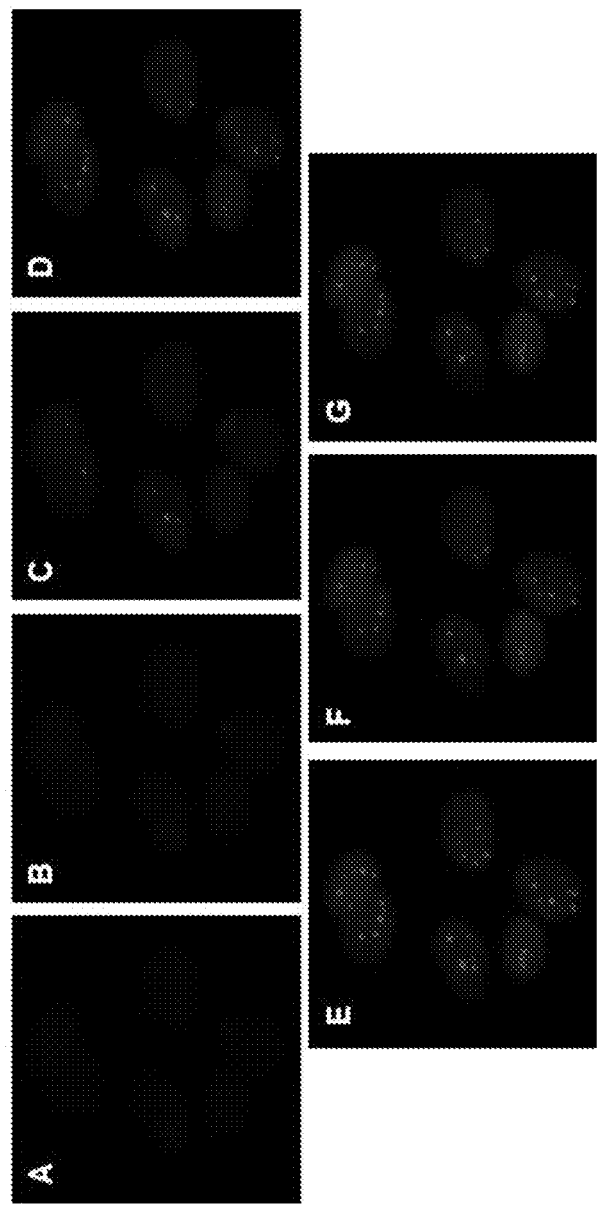
FIG. 9. Confocal imaging of RAD50 within the nuclei of a cluster of EMTCTCs from FIG. 1, imaged top to bottom. To verify the RAD50 loci are within the nuclear area of the cells, the cluster of EMTCTCs from FIG. 3 were imaged on a Zeiss confocal microscope.

Many groups have established that the formation of IRIF is observable by RAD50 foci formation in the nuclei of radiation damaged cells (FIG. 9)[18, 20, 23] and inhibition of IRIF formation though prior sensitization with DNA damaging stressors has been shown to be positively correlated with clinical outcome in a number of cancers (i.e. NSCLC, breast, squamous cell carcinoma etc.)[18, 20, 23, 24, 26]. We initially observed that untreated NSCLC patients prior to radiotherapy had low numbers of RAD50 foci with a significant rise in RAD50 foci directly in parallel with the induction of radiotherapy. This increase in RAD50 is likely a result of DNA damage caused by the radiotherapeutic induction and the RAD50 foci formation in circulating cells appears to act as a noninvasive tracer in cancer patients receiving site directed radiation therapy. We suggest that RAD50 could be used as in liquid biopsy analyses to confirm the organ of origin of circulating cells and suggests that both EMTCTCs and CAMLs disseminate from primary lung masses in patients.

The currently approved IHC testing of biopsy tissue for PD-L1 expression is only a predictor of response in patients with very high levels of PD-L1 expression, yet many PD-L1 negative patients will also benefit[29, 30, 33, 39-42, 46]. This discrepancy may be attributed to the dynamic nature of immune modulation expression and/or the inability to analyze the stromal cell components. Because immune checkpoint protein expression is dynamic, being influenced by multiple microenvironmental, inflammatory, and therapy factors, it has been hypothesized that blood based analysis may provide a more accurate representation of the current PD-L1 expression in patients[29, 30, 39, 42, 43, 47, 48]. Interestingly, we found three classes of PD-L1 responses in the circulating cells of patients, those that are persistently low, persistently high, or inducible from low to high; which occurs in about a third of patients (32%). This suggests that intrinsically high or inducible PD-L1 levels in nearly half of the patients (49%) could be predictive of immunotherapy response; a hypothesis that will need prospective validation in clinical trials that combine immunotherapy and radiotherapy.

Example 2

Tumor endothelial cells (TECs)[60-62] are a population of stromal cells required for tumor initiation, survival and growth by forming the vital structures for angiogenesis and neovascularization. TECs are mandatory constituents at all tumor sites, required for tumor vasculature, aid in priming metastatic niches, and contribute to the molecular instability of tumors. In the circulation, a common population of TECs has been identified and defined as cancer associated vascular endothelial cells (CAVEs) based on their large size, multicellular clustering, and the classical EC markers CD31 and Vimentin[60].

Size exclusion is a technique for isolating large cells from peripheral patient blood irrespective of their surface marker expression, allowing for the capture of many subtypes of circulating tumor ECs. CellSieve™ microfilters are size exclusion membranes capable of rapidly and efficiently isolating CAVEs, CAMLs and CTCs from whole blood, making it possible to study all cell types in conjunction with and in relation to malignant disease[13, 60-62]. Further, a multi-phenotyping technique has been developed using CellSieve™ microfilters allowing for a mass screening of subtyping biomarkers on isolated cells.

Figure 10:
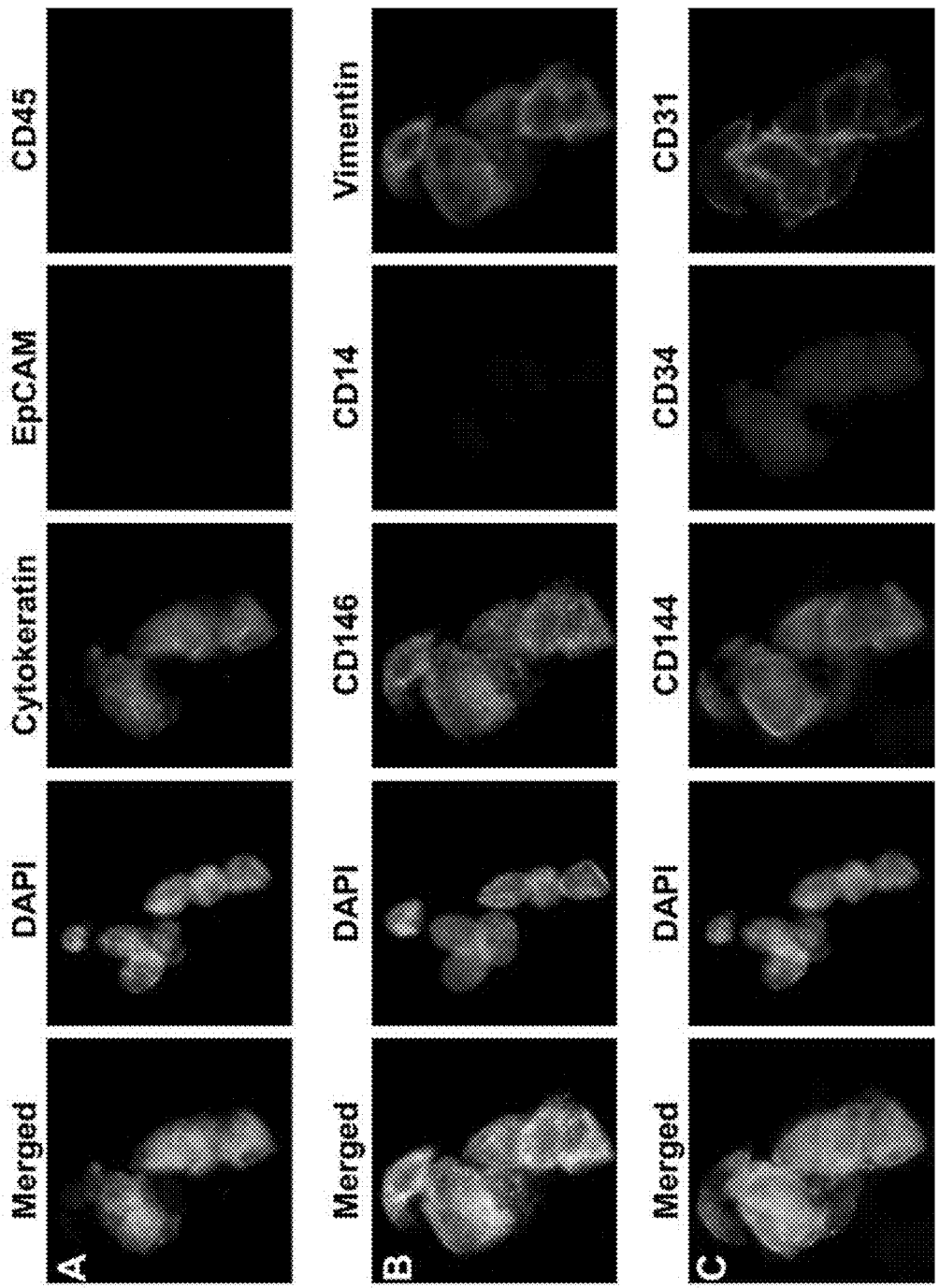
FIG. 10. Representative examples of cytokeratin positive CAVEs that stain positive for CD31 (FIG. 10C), CD146 (FIG. 10B), Vimentin (FIG. 10B), and CD144 (FIG. 10C), confirming their endothelial origin. All CAVEs are CD45 negative (FIG. 10A) and CD14 negative (FIG. 10B). This CAVE appears EpCAM negative (FIG. 10A), although some CAVEs have been found to express EpCAM.

To demonstrated this approach, peripheral blood samples from 116 cancer patients (stage I-IV) were drawn from 2012-2014 including breast (n=42), lung (n=39) and prostate (n=35), as well as blood from 34 healthy controls. Blood was processed by an established filtration approach, i.e. the CellSieve™ microfiltration technique (Creatv MicroTech), filtering blood by size exclusion and staining cells for CK 8, 18 & 19, EpCAM and CD45 (FIG. 10A). After identification and imaging, the QUAS-R (Quench, Underivatize, Amine-Strip and Restain) technique was used to remove fluorescence signal and restain all cells with CD146, CD14, vimentin, & DAPI (FIG. 10B). After reimaging, QUAS-R was again used to remove fluorescence and restain the cells for CD144, CD34 (or CD105), CD31, & DAPI (FIG. 10C). Multinucleated clusters of CAVEs were differentiated from cancer associated macrophage-like cells using CD14+ and the polyploid nucleus structure observed with CAMLs.

Figure 11:
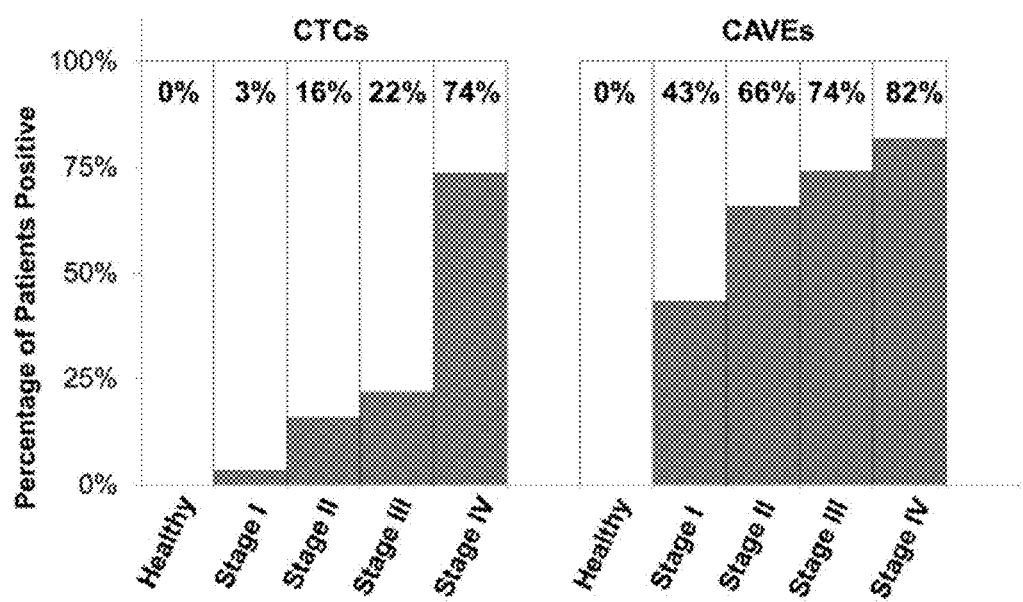
FIG. 11. Percentages of CTC and CAVEs in 116 patient sample by stage.

CAVEs were identified in 63 of 116 patients (54%) based on positivity of CD31, CD144 or CD146, but none were found in healthy controls. CAVEs were found in 43% of stage I, 66% of stage II, 74% of Stage III, and 82% of Stage IV patients (FIG. 11). CAVEs were found in 69% of breast, 60% lung, and 77% prostate samples.

Figure 12:
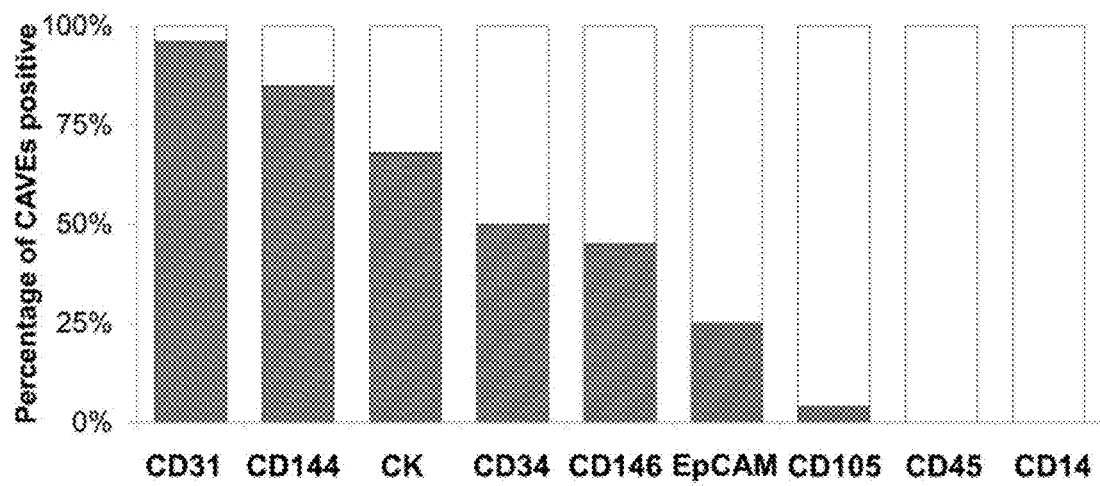
FIG. 12. Percentage of each EC marker on the CAVE population (n=119 samples).

CAVEs were all negative for CD14 and CD45. CD31 was the most present marker, found on 96% of CAVEs, followed by CD144 (85%), Cytokeratin (68%), CD34 (64%), CD146 (45%), EpCAM (23%)& CD105 (4%) (FIG. 12).

The results demonstrate that CECs isolated by microfiltration are positive for cytokeratin and negative for CD45 which appear commonly in the circulation of patients with solid tumors but not in healthy controls. Multi-phenotypic subtyping can properly identify and subtype CECs in cancer patients with multiple solid tumor types. This data suggests that a subset of CECs, e.g. CAVEs, are found in circulation as CK+/CD45− and exist as a heterogeneous population of cancer specific circulating cells.

Example 3

Figure 13:
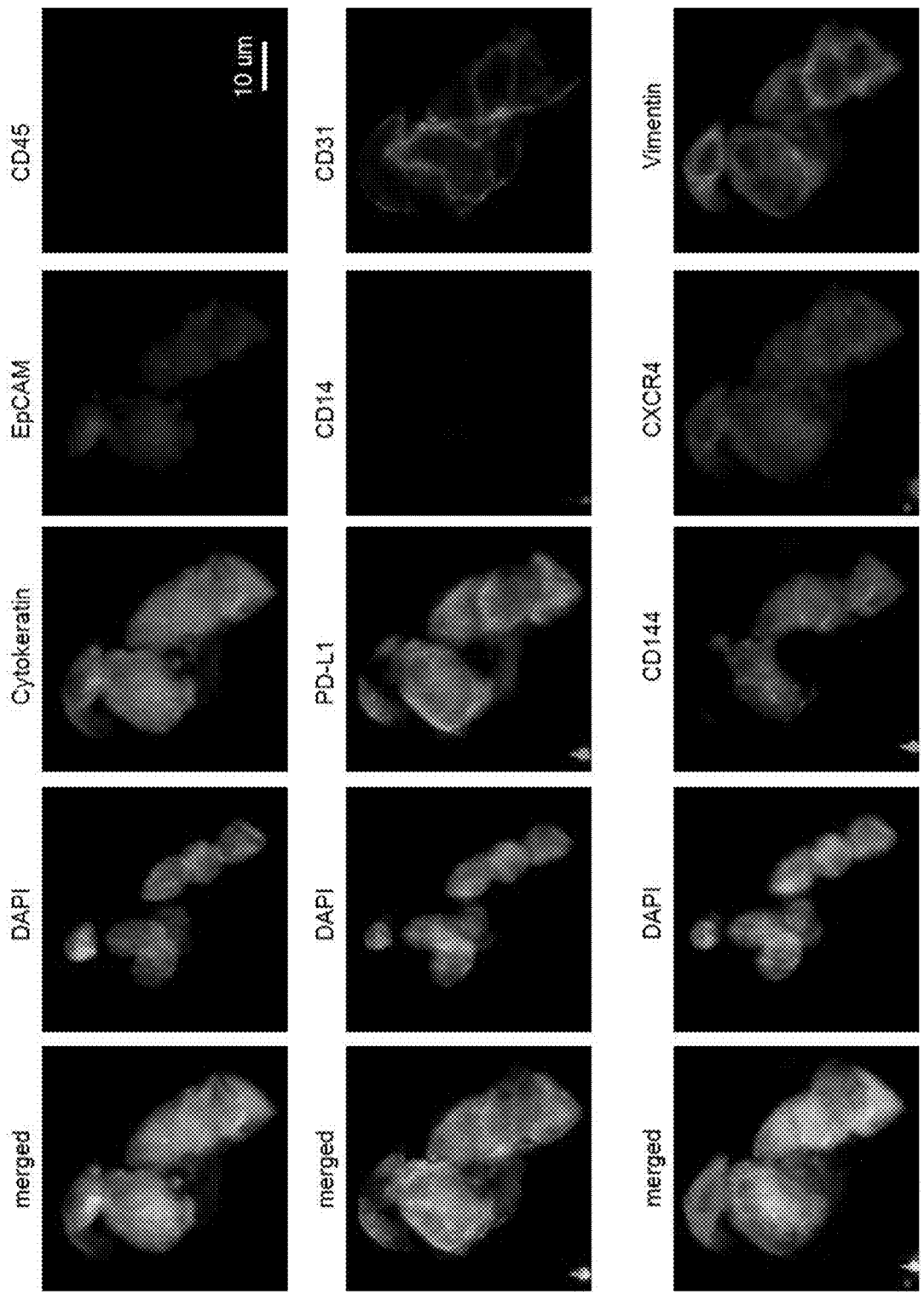
FIG. 13. Image of a cell cluster identified as CAVEs by staining. Additional staining illustrate capability of combination immunotherapy, PD-L1 and CXCR4.

FIG. 13 shows staining to verify CAVEs appearing in a cluster of cells. During the initial staining of all cells captured from a carcinoma patient, the samples were stained with DAPI, Cytokeratin 8, 18 & 19, EpCAM and CD45. The top row of FIG. 13 shows a cluster with Cytokeratin expression and EpCAM, no CD45 expression. The second row of FIG. 13 shows the cells were restained for DAPI, PD-L1, CD14 and CD31. CD31+ membrane staining and negative CD45 and CD14 staining indicates this is a CAVE cluster. This cluster of CAVEs has high expression of PD-L1. On the third row of FIG. 13, the cells were restained for CD144, CXCR4 and vimentin. CXCR4 is another drug target. QUAS-R was utilized for the restaining[13], which consisted of quenching the fluorescent dye followed by restaining. The restaining indicates a method for analyzing combination immunotherapy. In this example, both PD-L1 and CXCR4 expressions are high indicating that this combination immunotherapy might work for this patient.

Figure 14:
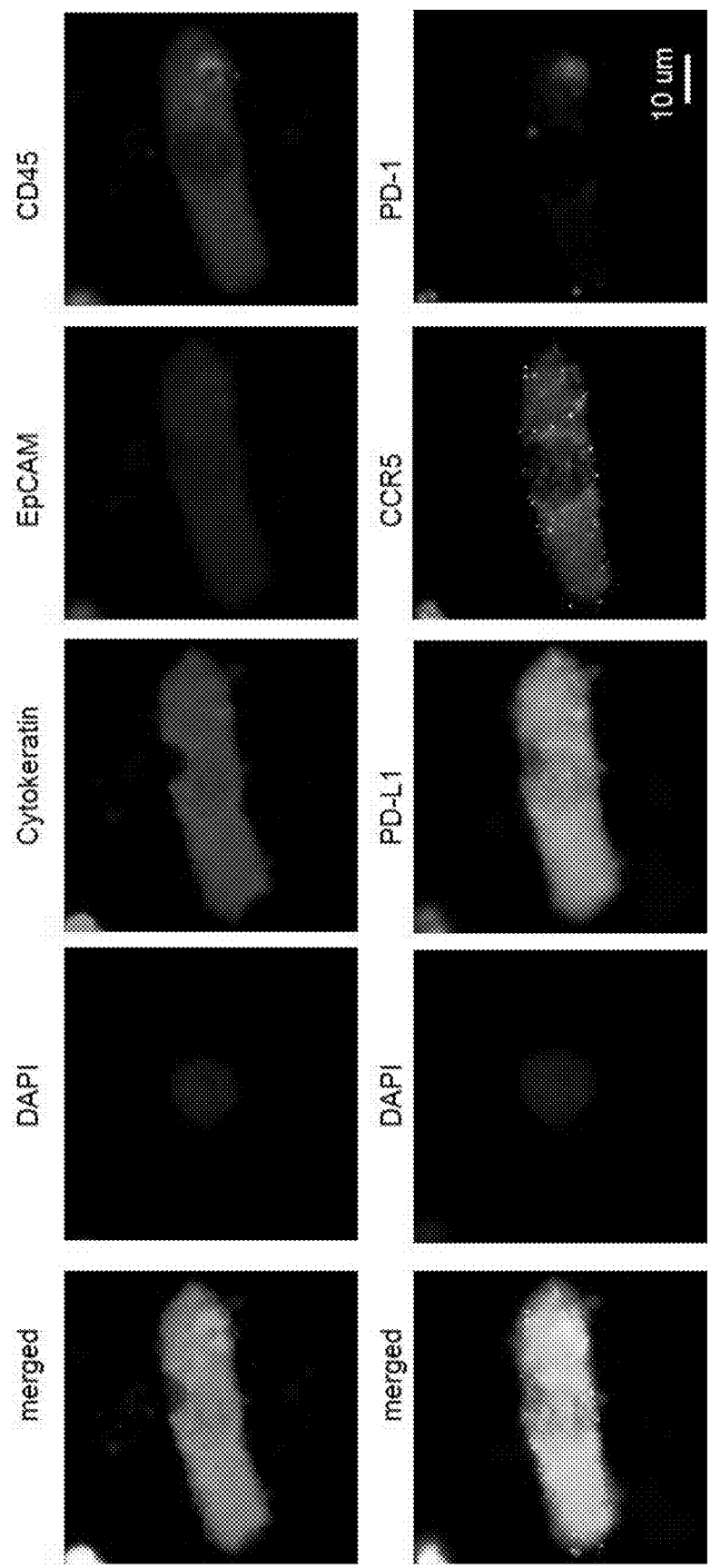
FIG. 14. Images of a CAML stained for combination immunotherapy, PD-L1 and CCR5.

FIG. 14 shows a CAML cell initially stained with DAPI, Cytokeratin 8, 18 & 19, EpCAM and CD45 (top row). The second row of FIG. 14 shows the cells were restained for DAPI, PD-L1, CCR5 and PD-1. In this example, both PD-L1 and CCR5 expressions are high indicating that this combination immunotherapy might work for this patient.

Figure 15:
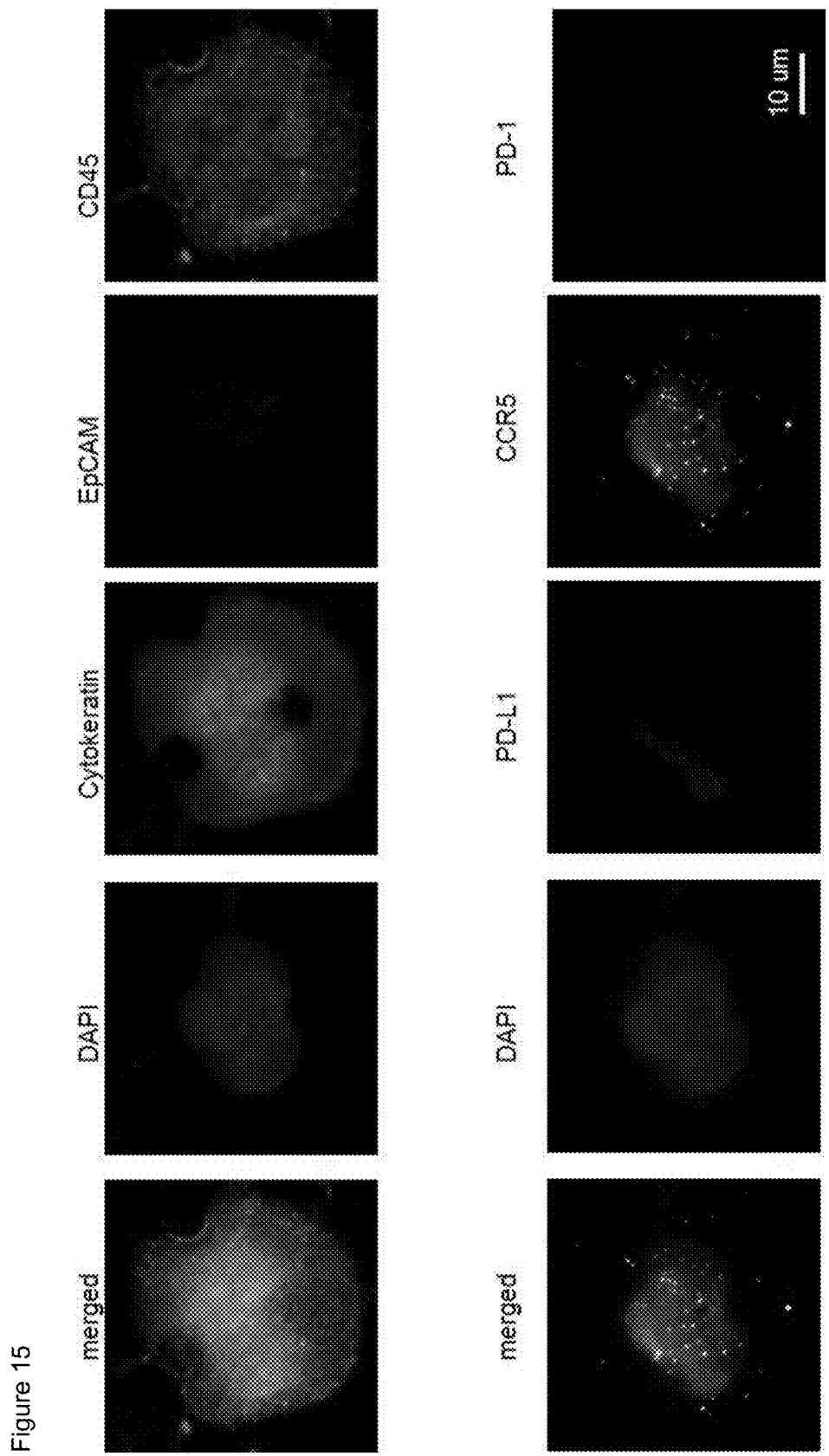
FIG. 15. Images of a CAML stained for PD-L1 and CCR5. There is a lack of staining for PD-L1.

FIG. 15 shows a CAML cell initially stained with DAPI, Cytokeratin 8, 18 & 19, EpCAM and CD45 (top row). The second row of FIG. 15 shows the cells were restained for DAPI, PD-L1, CCR5 and PD-1. In this example, there is CCR5 but no PD-L1 expressions indicating that this combination immunotherapy might work for this patient.

Example 4

A current companion diagnostic for immunotherapy is based on expression of PD-L1 protein on tissue biopsies. However, the IHC tissue biopsy approach is limited by the clinical feasibility and cost of repeating a biopsy, the inherent tumor heterogeneity, and knowledge that PD-L1 IHC negative patients may still respond to immunotherapy.

Expression of PD-L1 can be detected on CAMLs and CTCs, as shown in FIGS. 17A and 17B. To determine if PD-L1 expression can be monitored in real time from peripheral circulating cells, we evaluated serial samples from a patient with RCC pre- and post-initiation of pembrolizumab, an anti-PD1 immunotherapy. The PD-L1 expression was quantitatively measured and scored based on the fluorescence signal intensity: (signal-background)/background, or (S−N)/N. We demonstrated the ability to monitor the dynamic changes of PD-L1 protein expression during treatment using CAMLs.

Figure 16:
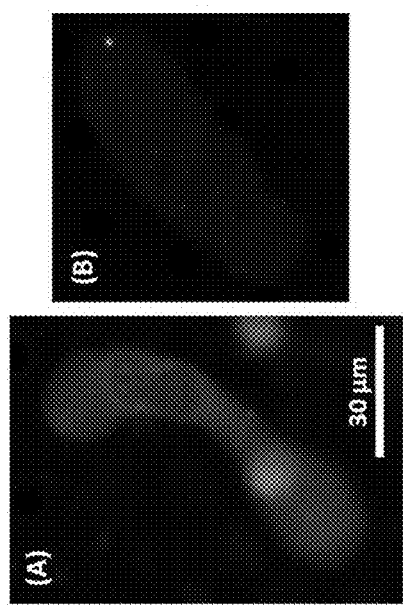
FIG. 16. Images of a CAML stained for PD-L1.

Before the first treatment with pembrolizumab for one patient, this expression was about 6 on the CAMLs (FIG. 16A). One month after pembrolizumab, the PD-L1 expression on the CAMLs dropped to the level of the background (FIG. 16B). FIG. 16B is a 74 μm long rod shaped CAML with (S−N)/N<0.5, nearly invisible in the PD-L1 fluorescent channel.

Figure 17:
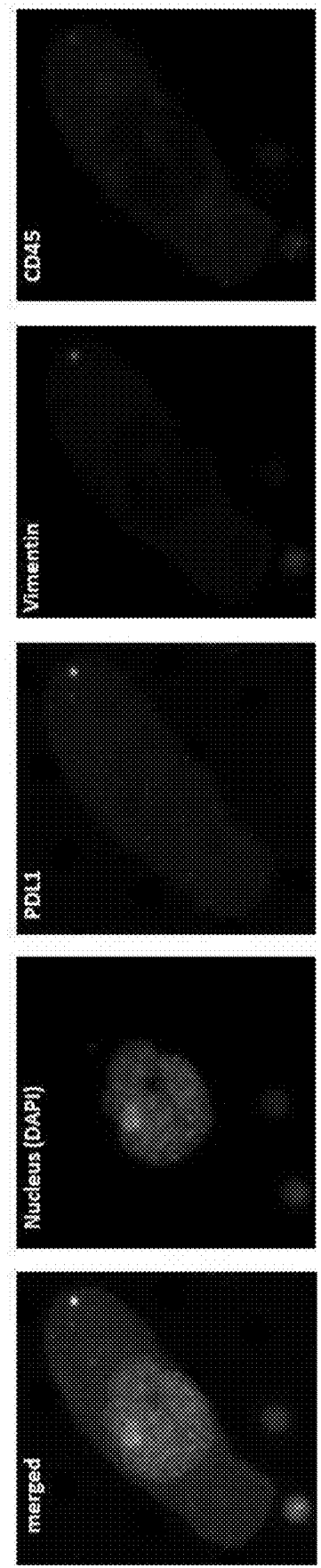
FIG. 17. Images of a CAML stained for nucleus, PD1, vimentin and CD45.

FIG. 17 includes other stains enabling the visualization of the cell. At this time the patient still had 26 CAMLs from one tube of blood, all with PD-L1 in the noise level. The patient died a few months later while still on pembrolizumab treatment. The loss of PD-L1 expression may indicate the presence of different RCC subclones or the selection of a PD-L1 low expressing subclone in response to pembrolizumab.

While the invention has been described with reference to certain particular embodiments thereof, those skilled in the art will appreciate that various modifications may be made without departing from the spirit and scope of the invention. The scope of the appended claims is not to be limited to the specific embodiments described.

REFERENCES

All patents and publications mentioned in this specification are indicative of the level of skill of those skilled in the art to which the invention pertains. Each cited patent and publication is incorporated herein by reference in its entirety. All of the following references have been cited in this application:

1. Adams D L, Zhu P, Makarova O V, Martin S S, Charpentier M, Chumsri S, et al. The systematic study of circulating tumor cell isolation using lithographic microfilters. RSC Advances. 2014; 4:4334-42.
2. Lianidou E S, Markou A. Circulating tumor cells in breast cancer: detection systems, molecular characterization, and future challenges. Clinical chemistry. 2011; 57:1242-55.
3. Pantel K, Brakenhoff R H, Brandt B. Detection, clinical relevance and specific biological properties of disseminating tumour cells. Nature reviews Cancer. 2008; 8:329-40.
4. Paterlini-Brechot P, Benali N L. Circulating tumor cells (CTC) detection: clinical impact and future directions. Cancer letters. 2007; 253:180-204.
5. Adams D, Tsai S, Makarova O V, Zhu P, Li S, Amstutz P T, et al. Low cytokeratin- and low EpCAM-expressing circulating tumor cells in pancreatic cancer. ASCO Annual Meeting Proceedings; 2013. p. 11046.
6. Adams D L, Stefansson S, Haudenschild C, Martin S S, Charpentier M, Chumsri S, et al. Cytometric characterization of circulating tumor cells captured by microfiltration and their correlation to the cellsearch((R)) CTC test.

Cytometry Part A: the journal of the International Society for Analytical Cytology. 2015; 87:137-144.

7. Krebs M G, Hou J M, Sloane R, Lancashire L, Priest L, Nonaka D, et al. Analysis of circulating tumor cells in patients with non-small cell lung cancer using epithelial marker-dependent and -independent approaches. J Thorac Oncol. 2012; 7:306-15.
8. Farace F, Massard C, Vimond N, Drusch F, Jacques N, Billiot F, et al. A direct comparison of CellSearch and ISET for circulating tumour-cell detection in patients with metastatic carcinomas. British journal of cancer. 2011; 105:847-53.
9. Lecharpentier A, Vielh P, Perez-Moreno P, Planchard D, Soria J C, Farace F. Detection of circulating tumour cells with a hybrid (epithelial/mesenchymal) phenotype in patients with metastatic non-small cell lung cancer. British journal of cancer. 2011; 105:1338-41.
10. Adams D L, Adams D K, Stefansson S, Haudenschild C, Martin S S, Charpentier M, et al. Mitosis in circulating tumor cells stratifies highly aggressive breast carcinomas. Breast cancer research: BCR. 2016; 18:44.
11. Adams D L, Adams D K, Alpaugh R K, Cristofanilli M, Martin S S, Chumsri S, et al. Circulating Cancer-Associated Macrophage-Like Cells Differentiate Malignant Breast Cancer and Benign Breast Conditions. Cancer Epidemiol Biomarkers Prev. 2016; 25:1037-42.
12. Adams D L, Alpaugh R K, Martin S S, Charpentier M, Chumsri S, Cristofanilli M, et al. Precision microfilters as an all in one system for multiplex analysis of circulating tumor cells. RSC Advances. 2016; 6:6405-14.
13. Adams D L, Alpaugh R K, Tsai S, Tang C M, Stefansson S. Multi-Phenotypic subtyping of circulating tumor cells using sequential fluorescent quenching and restaining. Sci Rep. 2016; 6:33488.
14. Adams D L, Martin S S, Alpaugh R K, Charpentier M, Tsai S, Bergan R C, et al. Circulating giant macrophages as a potential biomarker of solid tumors. Proceedings of the National Academy of Sciences of the United States of America. 2014; 111:3514-9.
15. Allard W J, Matera J, Miller M C, Repollet M, Connelly M C, Rao C, et al. Tumor cells circulate in the peripheral blood of all major carcinomas but not in healthy subjects or patients with nonmalignant diseases. Clin Cancer Res. 2004; 10:6897-904.
16. Anantharaman A, Friedlander T, Lu D, Krupa R, Premasekharan G, Hough J, et al. Programmed death-ligand 1 (PD-L1) characterization of circulating tumor cells (CTCs) in muscle invasive and metastatic bladder cancer patients. BMC Cancer. 2016; 16:744.
17. Mu Z, Benali-Furet N, Uzan G, Znaty A, Ye Z, Paolillo C, et al. Detection and Characterization of Circulating Tumor Associated Cells in Metastatic Breast Cancer. Int J Mol Sci. 2016; 17.
18. Abuzeid W M, Jiang X, Shi G, Wang H, Paulson D, Araki K, et al. Molecular disruption of RAD50 sensitizes human tumor cells to cisplatin-based chemotherapy. J Clin Invest. 2009; 119:1974-85.
19. Adams D L, Edelman M J, Fang P, Jiang W, He J, Xu T, et al. Sequential tracking of PD-L1 expression and RAD50 induction in CTCs and circulating stromal cells of lung cancer patients during treatment with radiotherapy. Cancer Research. 2016; 76:4990-.
20. Flores-Perez A, Rafaelli L E, Ramirez-Torres N, Arechaga-Ocampo E, Frias S, Sanchez S, et al. RAD50 targeting impairs DNA damage response and sensitizes human breast cancer cells to cisplatin therapy. Cancer Biol Ther. 2014; 15:777-88.
21. Garcia-Villa A, Balasubramanian P, Miller B L, Lustberg M B, Ramaswamy B, Chalmers J J. Assessment of gamma-H2AX levels in circulating tumor cells from patients receiving chemotherapy. Front Oncol. 2012; 2:128.
22. Lin S H, He J, Edelman M, Xu T, Gao H, Reuben J, et al. Sequential Assessment of DNA Damage Response and PD-L1 Expression in Circulating Tumor Cells of Lung Cancer Patients during Radiotherapy. JOURNAL OF THORACIC ONCOLOGY; 2015: ELSEVIER SCIENCE INC 360 PARK AVE SOUTH, NEW YORK, N.Y. 10010-1710 USA. p. S266-S7.
23. Maser R S, Monsen K J, Nelms B E, Petrini J H. hMre11 and hRad50 nuclear foci are induced during the normal cellular response to DNA double-strand breaks. Mol Cell Biol. 1997; 17:6087-96.
24. Wang L H, Pfister T D, Parchment R E, Kummar S, Rubinstein L, Evrard Y A, et al. Monitoring drug-induced gammaH2AX as a pharmacodynamic biomarker in individual circulating tumor cells. Clin Cancer Res. 2010; 16:1073-84.
25. Gatei M, Jakob B, Chen P, Kijas A W, Becherel O J, Gueven N, et al. A™ protein-dependent phosphorylation of Rad50 protein regulates DNA repair and cell cycle control. J Biol Chem. 2011; 286:31542-56.
26. Teng S C, Wu K J, Tseng S F, Wong C W, Kao L. Importin KPNA2, NBS1, DNA repair and tumorigenesis. J Mol Histol. 2006; 37:293-9.
27. Demaria S, Golden E B, Formenti S C. Role of Local Radiation Therapy in Cancer Immunotherapy. JAMA Oncol. 2015; 1:1325-32.
28. Derer A, Deloch L, Rubner Y, Fietkau R, Frey B, Gaipl U S. Radio-Immunotherapy-Induced Immunogenic Cancer Cells as Basis for Induction of Systemic Anti-Tumor Immune Responses—Pre-Clinical Evidence and Ongoing Clinical Applications. Front Immunol. 2015; 6:505.
29. Brahmer J, Reckamp K L, Baas P, Crino L, Eberhardt W E, Poddubskaya E, et al. Nivolumab versus Docetaxel in Advanced Squamous-Cell Non-Small-Cell Lung Cancer. N Engl J Med. 2015; 373:123-35.
30. Brahmer J R, Tykodi S S, Chow L Q, Hwu W J, Topalian S L, Hwu P, et al. Safety and activity of anti-PD-L1 antibody in patients with advanced cancer. N Engl J Med. 2012; 366:2455-65.
31. Garon E B, Rizvi N A, Hui R, Leighl N, Balmanoukian A S, Eder J P, et al. Pembrolizumab for the treatment of non-small-cell lung cancer. N Engl J Med. 2015; 372: 2018-28.
32. Gettinger S N, Horn L, Gandhi L, Spigel D R, Antonia S J, Rizvi N A, et al. Overall Survival and Long-Term Safety of Nivolumab (Anti-Programmed Death 1 Antibody, BMS-936558, ONO-4538) in Patients With Previously Treated Advanced Non-Small-Cell Lung Cancer. J Clin Oncol. 2015; 33:2004-12.
33. Ilie M, Long-Mira E, Bence C, Butori C, Lassalle S, Bouhlel L, et al. Comparative study of the PD-L1 status between surgically resected specimens and matched biopsies of NSCLC patients reveal major discordances: a potential issue for anti-PD-L1 therapeutic strategies. Annals of oncology: official journal of the European Society for Medical Oncology/ESMO. 2016; 27:147-53.
34. Reck M, Rodriguez-Abreu D, Robinson A G, Hui R, Csoszi T, Fulop A, et al. Pembrolizumab versus Chemotherapy for PD-L1-Positive Non-Small-Cell Lung Cancer. N Engl J Med. 2016.

35. Sundar R, Cho B C, Brahmer J R, Soo R A. Nivolumab in NSCLC: latest evidence and clinical potential. Therapeutic advances in medical oncology. 2015; 7:85-96.
36. Topalian S L, Hodi F S, Brahmer J R, Gettinger S N, Smith D C, McDermott D F, et al. Safety, activity, and immune correlates of anti-PD-1 antibody in cancer. N Engl J Med. 2012; 366:2443-54.
37. Antonia S, Goldberg S B, Balmanoukian A, Chaft J E, Sanborn R E, Gupta A, et al. Safety and antitumour activity of durvalumab plus tremelimumab in non-small cell lung cancer: a multicentre, phase 1b study. The lancet oncology. 2016; 17:299-308.
38. Borghaei H, Paz-Ares L, Horn L, Spigel D R, Steins M, Ready N E, et al. Nivolumab versus Docetaxel in Advanced Nonsquamous Non-Small-Cell Lung Cancer. N Engl J Med. 2015; 373:1627-39.
39. Ma W, Gilligan B M, Yuan J, Li T. Current status and perspectives in translational biomarker research for PD-1/PD-L1 immune checkpoint blockade therapy. J Hematol Oncol. 2016; 9:47.
40. Taube J M, Klein A, Brahmer J R, Xu H, Pan X, Kim J H, et al. Association of PD-1, PD-1 ligands, and other features of the tumor immune microenvironment with response to anti-PD-1 therapy. Clin Cancer Res. 2014; 20:5064-74.
41. Herbst R S, Soria J C, Kowanetz M, Fine G D, Hamid O, Gordon M S, et al. Predictive correlates of response to the anti-PD-L1 antibody MPDL3280A in cancer patients. Nature. 2014; 515:563-7.
42. Ung C, Kockx M M. Challenges & Perspectives of Immunotherapy Biomarkers & The HistoOncoImmune™ Methodology. Expert Review of Precision Medicine and Drug Development. 2016; 1:9-24.
43. Zhu P, Stanton M L, Castle E P, Joseph R W, Adams D L, Li S, et al. Detection of tumor-associated cells in cryopreserved peripheral blood mononuclear cell samples for retrospective analysis. J Transl Med. 2016; 14:198.
44. Alix-Panabieres C, Pantel K. Challenges in circulating tumour cell research. Nature reviews Cancer. 2014; 14:623-31.
45. Marrinucci D, Bethel K, Kolatkar A, Luttgen M S, Malchiodi M, Baehring F, et al. Fluid biopsy in patients with metastatic prostate, pancreatic and breast cancers. Phys Biol. 2012; 9:016003.
46. Callahan M K, Ott P A, Odunsi K, Bertolini S V, Pan L S, Venhaus R R, et al. A phase 1 study to evaluate the safety and tolerability of MEDI4736, an anti-PD-L1 antibody, in combination with tremelimumab in patients with advanced solid tumors. ASCO Annual Meeting Proceedings; 2014. p. TPS3120.
47. Mazel M, Jacot W, Pantel K, Bartkowiak K, Topart D, Cayrefourcq L, et al. Frequent expression of PD-L1 on circulating breast cancer cells. Mol Oncol. 2015; 9:1773-82.
48. Satelli A, Batth I S, Brownlee Z, Rojas C, Meng Q H, Kopetz S, et al. Potential role of nuclear PD-L1 expression in cell-surface vimentin positive circulating tumor cells as a prognostic marker in cancer patients. Sci Rep. 2016; 6:28910.
49. Nicolazzo C, Raimondi C, Mancini M, Caponnetto S, Gradilone A, Gandini O, et al. Monitoring PD-L1 positive circulating tumor cells in non-small cell lung cancer patients treated with the PD-1 inhibitor Nivolumab. Sci Rep. 2016; 6:31726.
50. Daniel L. Adams, R. Katherine Alpaugh, Steven H. Lin, Jeffrey R. Marks, Raymond Bergan, Stuart S. Martin, Saranya Chumsri, Massimo Cristofanilli, Cha-Mei Tang, Steingrimur Stefansson, "Multiplex phenotyping of circulating cancer associated macrophage-like cells in patients with solid tumors", Proceedings of AACR, Vol. 58, April 2017. Abstract #778.
51. American Cancer Society. http://www.cancer.org/cancer/cancerbasics/lifetime-probability-of-developing-or-dying-from-cancer
52. SEER. https://seer.cancer.gov/
53. CDC. https://www.cdc.gov/nchs/fastats/leading-causes-of-death.htm
54. Burstein H J, Krilov L, Aragon-Ching J B, Baxtert N N, Chiorean E G, Chow W N, De Groot J F, Devine S M, and more, Clinical Cancer Advances 2017: Annual Report on Progress Against Cancer From the American Society of Clinical Oncology. J. of Clinical Oncology, 2017, Feb. 1, 35. DOI: 10.1200/JC0.2016.71.5292. http://ascopubs.org/doi/abs/10.1200/JCO.2016.71.5292
55. Yervoy (ipilimumab) FDA approval history. https://www.drugs.com/history/yervoy.html
56. Opdivo (nivolumab) FDA approval history. https://www.drugs.com/history/opdivo.html
57. Keytruda (pembrolizumab) FDA approval history. https://www.drugs.com/history/keytruda.html
58. Tecentriq (atezolizumab) FDA approval history. https://www.drugs.com/history/tecentriq.html
59. Yervoy and Opdivo combination FDA approval history. http://www.fda.gov/Drugs/InformationOnDrugs/ApprovedDrugs/ucm465274.htm
60. Adams D L "Detection and monitoring of circulating immune cells in solid tumors: shifting priorities In liquid biopsies in solid tumors" (Chapter 5), Springer, 2017.
61. El-Heliebi A, et al "Are morphological criteria sufficient for the identification of circulating tumor cells in renal cancer?" J. Trans Med. 11:214, 2013
62. Cima I, et al "Tumor-derived circulating endothelial cell clusters in colorectal cancer." Sci Trans Med 8(345): 345ra389 2016.

What is claimed is:

1. A method of treating a subject having cancer, comprising:
   (a) assaying circulating tumor cells (CTCs) and cancer associated macrophage-like cells (CAMLs), and optionally one or more of epithelial to mesenchymal transition CTCs (EMTCTCs) and cancer associated vascular endothelial cells (CAVEs), isolated from a subject having cancer for PD-L1 expression, and
   (b) administering a therapeutically effective amount of an immune checkpoint inhibitor to the subject when PD-L1 expression is detected,
      wherein the immune checkpoint inhibitor is one or more of Nivolumab, Ipilimumab, Pembrolizumab, Atezolizumab, Tremelimumab, and Durvalumab.

2. The method of claim 1, further comprising administering a therapeutically effective amount of one or more additional anti-cancer agents to the subject.

3. The method of claim 2, wherein the one or more additional anti-cancer agents are selected from the group consisting of immunotherapeutic agents, chemotherapeutic agents, radiotherapeutic agents, existing cancer drugs, CCR5 and CXCR4.

4. The method of claim 2, wherein the one or more additional anti-cancer agents are selected from the group consisting of T-VEC, AM-0010, CXCR4 antagonist, TGF-beta kinase inhibitor galunisertib, anti-CSF-1R monoclonal antibody, Abemaciclib, Faslodex, necitumumab, AZD9291, ramucirumab, TPIV 200, Galunisertib, cancer vaccines, cytokines, cell-based therapies, bi- and multi-specific antibodies, tumor-2 targeting mAbs, Rituximab, oncolytic viruses, reovirus, Blinatumomab, Sipuleucel-T, T-Vec, IL-2, IFN-a, Trastuzumab, Celuximab, bevacizumab, Tim-3, BTLA, anti-IL-10, GM-CSF, anti-angiogenesis treatment, VEGF blockade, HMGB1, NrpI, TAM receptor tyrosine kinases, Axl, MerTK, ALT-803, IL-15, Immunosuppressive Ligand Phosphatidylserine (PS), bavituximab, bevacizumab (anti-VEGF), coblmetinib (MEK inhibitor), vemurafenib (BRAF inhibitor), erlotinib (EGFR), alectinib (ALK inhibitor), bevacizumab (anti-VEGF), pazopanib (tyrosine kinase inhibitor), dabrafenib (BRAF inhibitor), trametinib (MEK inhibitor), durvalumab (anti-PD-L1), sunitinib (RTK inhibitor), pazopanib (RTK inhibitor), sargramostim, VISTA, TIM-3, LAG-3, PRS-343, CD137 (4-1 BB)/HER2 bispecific, USP7, anti-HER2, SEMA4D, CTLA-4, PD-i, PD-L1, and PD-L2.

5. The method of claim 1, wherein the assaying for PD-L1 expression is by one or more of detecting PD-L1 protein expression and detecting PD-L1 mRNA production.

6. The method of claim 5, wherein the PD-L1 protein expression is detected via immunohistochemistry (IHC).

7. The method of claim 6, wherein IHC is performed using an anti-PD-L1 antibody.

8. The method of claim 6, wherein IHC is performed using immunofluorescence (IF) staining, wherein one or more antibodies with binding specificity for PD-L1 are utilized.

9. The method of claim 8, wherein binding of the anti-PD-L1 antibody to PD-L1 is detected via a fluorescent compound conjugated to the anti-PD-L1 antibody or via a fluorophore-conjugated secondary antibody with binding specificity for the anti-PD-L1 antibody.

10. The method of claim 1, wherein PD-L1 expression is detected when the level of PD-L1 expression is greater than PD-L1 expression in a population of stromal cells from a subject of the same species that does not have cancer.

11. The method of claim 1, wherein CTCs, EMTCTCs, CAMLs, and CAVEs are isolated from a bodily fluid obtained from the subject having cancer.

12. The method of claim 1, wherein the cancer is a solid tumor.

13. The method of claim 12, wherein the solid tumor is a carcinoma, sarcoma, neuroblastoma or melanoma.

14. The method of claim 1, wherein the cancer is lung cancer, breast cancer, prostate cancer, pancreatic cancer, melanoma, bladder cancer, kidney cancer, head and neck cancer, colorectal cancer, liver cancer, ovarian cancer, neuroblastoma, sarcoma, osteosarcoma, esophageal, brain & ONS, larynx, bronchus, oral cavity and pharynx, stomach, testis, thyroid, uterine cervix, or uterine corpus cancer.

15. The method of claim 1, wherein at least one CTC, EMT cell, CAML, or CAVE exhibits at least one RAD50 foci after radiation treatment.

16. The method of claim 11, wherein the bodily fluid is blood.

17. The method of claim 11, wherein the cells are isolated from the bodily fluid via a microfiltration assay using a low-pressure vacuum system.

* * * * *